(12) United States Patent
Yan et al.

(10) Patent No.: US 9,085,530 B2
(45) Date of Patent: Jul. 21, 2015

(54) METHODS FOR SYNTHESIZING 3-(SUBSTITUTED DIHYDROISOINDOLINONE-2-YL)-2, 6-DIOXOPIPERIDINE, AND INTERMEDIATES THEREOF

(75) Inventors: Rong Yan, Jiangsu (CN); Hao Yang, Jiangsu (CN); Yongxiang Xu, Jiangsu (CN)

(73) Assignees: Nanjing Cavendish Bio-Engineering Technology Co., Ltd., Nanjing, iangsu (CN); Rong Yan, Nanjing, Jiangsu (CN)

( * ) Notice: Subject to any disclaimer, the term of this patent is extended or adjusted under 35 U.S.C. 154(b) by 96 days.

(21) Appl. No.: 13/375,610

(22) PCT Filed: Jun. 1, 2010

(86) PCT No.: PCT/CN2010/073437
§ 371 (c)(1), (2), (4) Date: Dec. 1, 2011

(87) PCT Pub. No.: WO2010/139266
PCT Pub. Date: Dec. 9, 2010

(65) Prior Publication Data
US 2012/0077982 A1    Mar. 29, 2012

(30) Foreign Application Priority Data
Jun. 1, 2009   (CN) .......................... 2009 1 0142160

(51) Int. Cl.
C07D 401/04 (2006.01)
C07D 209/48 (2006.01)
C07D 209/46 (2006.01)
C07D 405/04 (2006.01)

(52) U.S. Cl.
CPC ............ C07D 209/46 (2013.01); C07D 209/48 (2013.01); C07D 401/04 (2013.01); C07D 405/04 (2013.01)

(58) Field of Classification Search
CPC ... C07D 209/46; C07D 401/04; C07D 405/04
USPC .................. 546/201; 548/472, 465
See application file for complete search history.

(56) References Cited

U.S. PATENT DOCUMENTS

| | | | |
|---|---|---|---|
| 5,874,448 A * | 2/1999 | Muller et al. ................ | 514/323 |
| 6,380,239 B1 | 4/2002 | Muller et al. | |
| 6,534,651 B2 * | 3/2003 | Jagtap et al. ................ | 544/144 |
| 7,153,867 B2 * | 12/2006 | Shah et al. .................. | 514/323 |
| 7,405,237 B2 * | 7/2008 | Muller et al. ................ | 514/416 |
| 7,569,597 B2 * | 8/2009 | Muller et al. ................ | 514/414 |
| 7,816,393 B2 * | 10/2010 | Muller et al. ................ | 514/414 |
| 7,863,451 B2 * | 1/2011 | Muller et al. ................ | 546/201 |
| 7,994,327 B2 | 8/2011 | Ge et al. | |
| 2006/0160854 A1 | 7/2006 | Muller et al. | |

FOREIGN PATENT DOCUMENTS

| | | |
|---|---|---|
| CN | 101031545 A | 9/2007 |
| CN | 101080400 A | 11/2007 |
| CN | 101253163 A | 8/2008 |
| EP | 480745 | * 11/1991 |
| EP | 0641776 A2 | 3/1995 |
| JP | 62-195380 | * 8/1987 |
| JP | 5-92977 | 4/1993 |
| JP | 2001-503384 A | 3/2001 |
| JP | 2002506068 A | 2/2002 |
| JP | 2002-539197 A | 11/2002 |
| JP | 2008-544993 A | 12/2008 |
| JP | 2009-102621 A | 5/2009 |
| KR | 100672892 B1 | 1/2007 |
| WO | 9119700 A1 | 12/1991 |
| WO | 9414448 A1 | 7/1994 |
| WO | 9803502 A1 | 1/1998 |
| WO | 9946258 A1 | 9/1999 |
| WO | 0055134 A1 | 9/2000 |
| WO | 02059106 A1 | 8/2002 |
| WO | 2005105088 A2 | 11/2005 |
| WO | 2006028964 A1 | 3/2006 |

OTHER PUBLICATIONS

Japtap et al. "Preparation of . . . " CA135:304105 (2001).*
Guo et al. "Preparation of tartaric . . . " CA144:69727 (2005).*
Balwin et al. "preparation of . . . " CA117:69850 (1992).*
Narita et al. "Preparation of piperazinyl . . . " CA108:37868 (1988).*
Bruce et al. "The selectivity of reversible . . . " J. Am. Chem. Soc. 122 p. 9674-9684 (2000).*
Byers et al."Tandem radical . . . " Tetrhedron Lett, 45, p. 6587-6590(2004).*

(Continued)

Primary Examiner — Celia Chang
(74) Attorney, Agent, or Firm — MacMillan, Sobanski & Todd, LLC

(57) ABSTRACT

The present invention discloses methods for synthesizing 3-(substituted dihydroisoindolinone-2-yl)-2,6-dioxopiperidine and intermediates thereof, namely, the synthesis of compounds of the Formula (I), with each substitutional group defined in the patent specification. Owing to the advantages of high productivity, little influence to the environment and material accessibility, the methods of the present invention is suitable for industrial production.

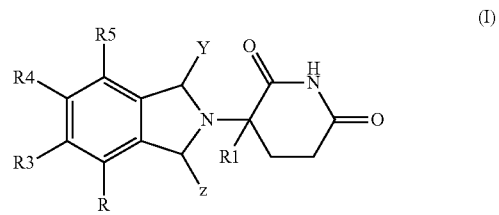

1 Claim, No Drawings

(56) References Cited

OTHER PUBLICATIONS

Kerton et al. "Alternative solvents . . . " p. 16 (2013).*
Laue et al. "Named Organic reactions" p. 56-57 (2005).*
Wang et al. "Synthesis of enantiopure . . ." Tetrahedron: asymmetry 12 p. 725-730 (2001).*
Pendergast, et al., "Benzo[f]quinazoline Inhibitors of Thymidylate Synthase: Methyleneamino-Linked Aroylglutamate Derivatives", Journal of Medicinal Chemistry, 1994, vol. 37, pp. 838-844.
Rosowsky, et al., "Synthesis and in Vitro Antifolate Activity of Rotationally Restricted Aminopterin and Methotrexate Analogues", Journal of Medicinal Chemistry, 2004, vol. 47, pp. 6958-6963.
Shao, et al., "Potential Anticancer Agents—synthesis of Derivatives of N-phthalylglutamine and Related Compound", Yaoxue Xuebao, 1996, vol. 13, No. 1, pp. 14-23.
Taylor, et al., "Synthesis of Conformationally-Constrained Glutamate Analogues of the Antitumor Agetns DDATHF, LY254155, and LY231514", Journal of Organic Chemistry, 1997, vol. 62, pp. 5392-5403.
International Search Report, Application No. PCT/CN2010/073437, dated Sep. 16, 2010.
Caswell, et al., "Nitrophthaloyl and Aminophthaloyl Derivatives of Amino Acids", Journal of Chemical and Engineering Data, Apr. 1968, vol. 13, No. 2, pp. 291-292.
De, et al., "Possible Antineoplastic Agents I", Journal of Pharmaceutical Sciences, Feb. 1975, vol. 64, No. 2, pp. 262-266.
Muller, et al., "Amino-Substituted Thalidomide Analogs: Potent Inhibitors of TNF-α Production", Bioorganic & Medicinal Chemistry Letters, 1999, vol. 9, pp. 1625-1630.
Rosowsky, et al., "5-Deazafolate Analogues with a Rotationally Restricted Glutamate or Ornithine Side Chain: Synthesis and Binding Interaction with Folylpolyglutamate Synthetase", Journal of Medicinal Chemistry, 1999, vol. 42, No. 18, pp. 3510-3519.
Muller et al., "Amino-Substituted Thalidomide Analogs: Potent Inhibitors of TNF-α Production", Bioorganic & Medicinal Chemistry Letters, 1999, vol. 9, pp. 1625-1630.
Kloster-Jensen, "Synthesis of 4-Bromophthalyl-D,L-glutamic Imide", Acta Chemica Scandinavica, 1965, vol. 19, No. 1, pp. 266-267.

* cited by examiner

METHODS FOR SYNTHESIZING 3-(SUBSTITUTED DIHYDROISOINDOLINONE-2-YL)-2,6-DIOXOPIPERIDINE, AND INTERMEDIATES THEREOF

CROSS-REFERENCE TO RELATED APPLICATIONS

This application is the National Phase of International Application PCT/CN2010/073437 filed Jun. 1, 2010, which designated the U.S. That International Application was published in English under PCT Article 21(2) on Dec. 9, 2010 as International Publication Number WO 2010/139266A1. PCT/CN2010/073437 claims priority to Chinese Application No. 200910142160.9 filed Jun. 1, 2009. Thus, the subject nonprovisional application also claims priority to Chinese Application No. 200910142160.9 filed Jun. 1, 2009. The disclosures of both applications are incorporated herein by reference.

TECHNICAL FIELD

The present invention is in the field of pharmaceutical chemistry, and more specifically it relates to methods for synthesizing 3-(substituted dihydroisoindolinone-2-yl)-2,6-dioxopiperidine, and intermediates thereof.

BACKGROUND ART

Lenalidomide, an analog of Thalidomide, is a kind of immunomodulator with anti-vascular proliferation and anti-tumor activities; its chemical name is 3-(4-amino-1-oxo-1,3-dihydro-2H-isoindol-2-yl)-2,6-dioxopiperidine and its chemical structure is as following:

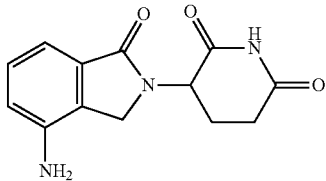

Lenalidomide has the residue of dioxopiperidine and dihydroisoindoline residue, as well as an asymmetric center in its structure. At present Lenalidomide approved on the market are racemic mixtures.

As is manifest in the article "Amino-substituted thalidomide analogs: Potent inhibitors of TNF-α production" (Bioorganic & Medicinal Chemistry Letters, Vol. 9, Issue 11, 7 Jun. 1999, pp 1625-1630) and the Chinese Patent ZL97180299.8 by Muller etc., the method of preparing 3-(substituted dihydroisoindolinone-2-yl)-2,6-dioxopiperidine is as following: α-aminoglutarimide hydrochloride reacts with methyl 2-bromomethyl-3-nitrobenzoate, then hydrogenated over Pd/C to yield lenalidomide.

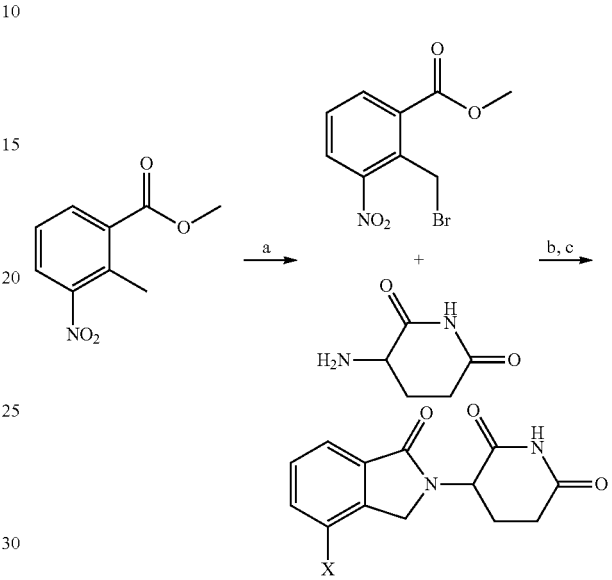

wherein, (a) under ultraviolet light (mercury lamp), NBS, $CCl_4$, refluxing; (b) $Et_3N$, DMF, 80° C.; (c) $H_2$, 10% Pd/C, MeOH. 7a X=4-$NO_2$, 8a X=4-$NH_2$. In which, the synthesis of α-aminoglutarimide hydrochloride begins with N-benzyloxycarbony-L-glutamine which reacts with N,N'-carbonyldiimidazole (CDI) refluxing in THF to yield N-benzyloxycarbony-aminoglutarimide; the key material of the reaction is: methyl 2-bromomethyl-3-nitro benzoate, which is converted from 2-methyl-3-nitrobenzoate by catalytic bromination in the condition of carbon tetrachloride under ultraviolet light. The catalytic and refluxing reaction needs long time and the yield is low. Additionally, the mass production is unease to be realized due to the difficulty of workers' labour protection against ultraviolet produced by mercury lamp as catalytic light source.

In the US Patent application US2006/0052609 A1, Muller etc. disclosed another synthetic method of 3-(substituted dihydroisoindolinone-2-yl)-2,6-dioxopiperidine:

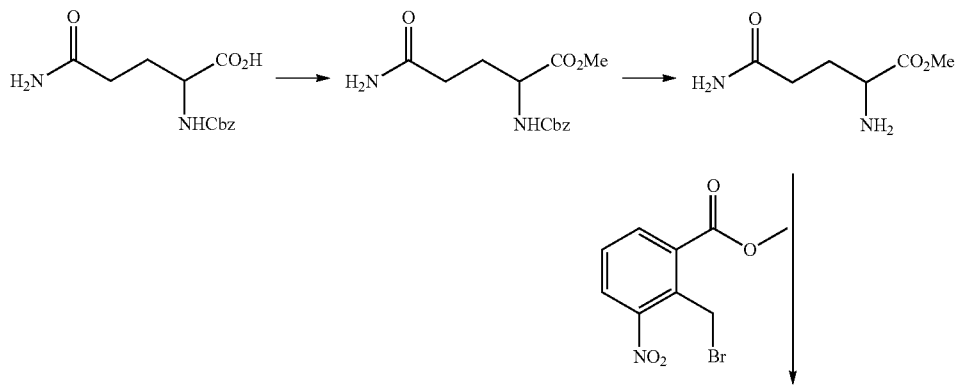

-continued

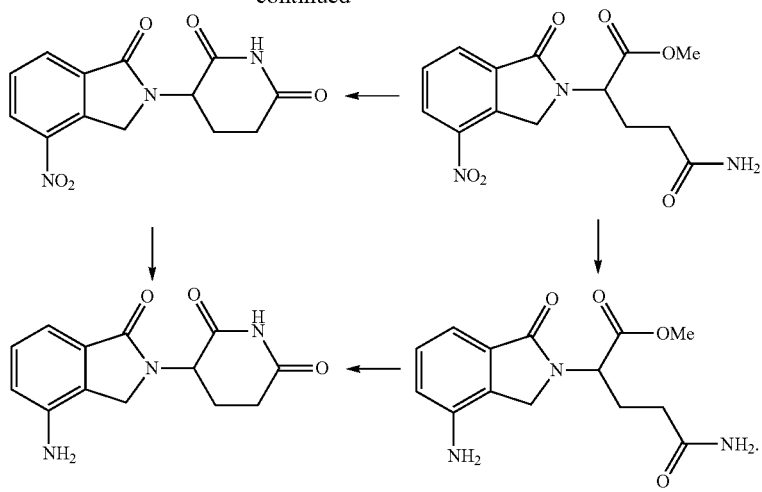

In the US Patent application US2006052609A1 and the Chinese Patent application CN97180299.8, the reaction product was purified by column chromatography at least twice or more, which made industrial operation complicated and made it difficult to industrial scale-up production.

In the US Patent application US2006052609A1 and the Chinese Patent application CN97180299.8, pressurized hydrogenation was both utilized twice, which was of much more risk in industrial operation.

In addition, when N-benzyloxycarbony-L-glutamine, as initial material, reacted with N,N'-carbonyldiimidazole in THF refluxing for 24 h to yield N-benzyloxycarbony-amino-glutarimide, low purity of yield due to long reactive time for refluxing and high temperature made extraction difficult.

On the other hand, the total yield was lower than 20% and 18% respectively reported in the US Patent application US2006052609A1 and the Chinese Patent application. Also, in the above two documents "lethal carbon tetrachloride" was reported to be reactive solvent used for refluxing. Carbon tetrachloride had serious destruction to ozone layer, which was forbidden to use by UNEP. Because of the high toxicity of carbon tetrachloride, it was difficult to dispose this substance, which is harmful to environment.

SUMMARY OF INVENTION

The present invention provides a novel method for synthesizing 3-(substituted dihydroisoindolinone-2-yl)-2,6-dioxopiperidine and its intermediates, which overcame the disadvantages mentioned above in prior art.

One objective of the present invention is to provide a novel method for synthesizing 3-(substituted dihydroisoindolinone-2-yl)-2,6-dioxopiperidine.

Another objective of the present invention is to provide the intermediates used to synthesize 3-(substituted dihydroisoindolinone-2-yl)-2,6-dioxopiperidine.

DETAILED DESCRIPTION OF INVENTION

In one embodiment of the present invention, a novel method for synthesizing the compound of Formula (I) is provided.

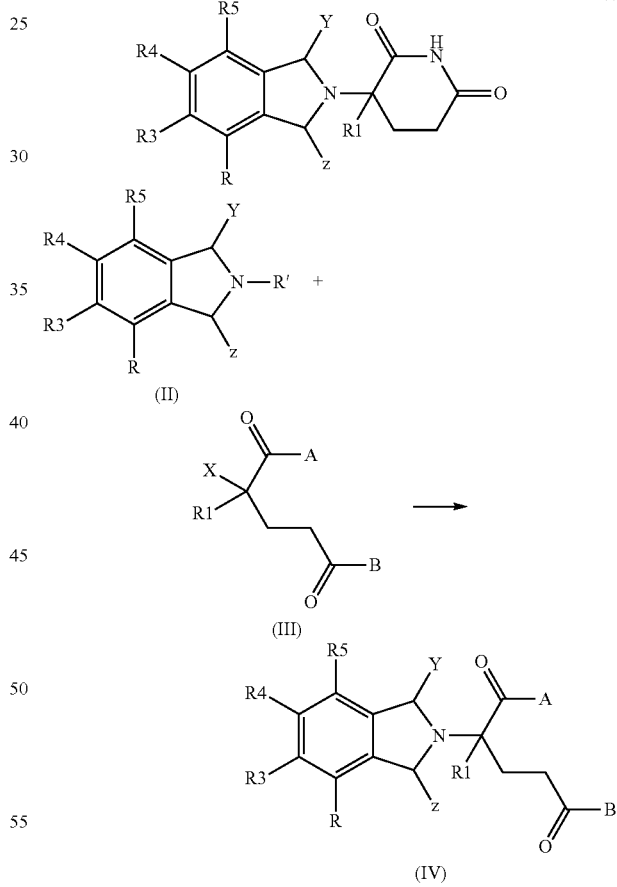

Including the reaction of the compound of Formula (II) and the compound of Formula (III) to yield the compound of Formula (IV);

wherein:

One of R, R3, R4 and R5 is amino or protected amino (carbamates: such as carbobenzyloxy, t-butyloxycarbonyl, fluorenylmethoxycarbonyl, etc.; acyl amides: such as acetyl, phenylacetyl, phthalyl, etc.; azanes: such as allyl, etc.; sulfonyl and sulfinyl: such as phenylsulfonyl, p-toluenesulfonyl, phenylsulfinyl, O-nitrophenylsulfinyl, etc.; referred to Greene T. W. and WuTs P. G. M. *Protective Groups in Organic Synthesis: P494-*; East China University Of Science And Technology Press, which is hereby incorporated by reference in their entirety), nitro or halo (for example F, Cl, Br or I), and the others are all hydrogen, preferably, R3, R4 and R5 are hydrogen;

X is halo, such as: F, Cl, Br or I;

Y is =O or H;

Z is =O or H;

with the proviso that Y and Z are both =O; or one of Y and Z is =O and the other of Y and Z is H;

R' is alkali metal ion or hydrogen (such as: H, $Li^+$, $Na^+$, $K^+$ or $Cs^+$), or imine protecting group (such as ethoxycarbonyl, etc.; referred to Greene T. W. and WuTs P. G. M. *Protective Groups in Organic Synthesis*: P494-, East China University Of Science And Technology Press, and *Chemical Research and Application*: 2006, 18(11): 1349-1352), etc., preferably $K^+$ or $Cs^+$, and more preferably $Cs^+$;

A and B are each independently hydroxyl, $C_{1-10}$ alkoxy, aryloxy, aryl $C_{1-4}$ alkoxy or $NHR_2$, and herein, $R_2$ is hydrogen or amino protecting group (carbamates: such as carbobenzyloxy, t-butyloxycarbonyl, fluorenylmethoxycarbonyl, etc.; acyl amides: such as acetyl, phenylacetyl, phthalyl, etc.; azanes: such as allyl, etc.; sulfonyl and sulfinyl: such as phenylsulfonyl, p-toluenesulfonyl, phenylsulfiny, O-nitrophenylsulfinyl, etc.; referred to *Protective Groups in Organic Synthesis*: Greene T. W., WuTs P. G. M. East China University Of Science And Technology Press: P494-); preferably, A and B are each independently hydroxyl, methoxyl, ethoxyl, propoxy, isopropoxy, butoxy, isobutoxy, t-butoxy, pentyloxy, hexyloxy, heptyloxy, octyloxy, nonyloxy, decyloxy; phenoxy or substituted phenoxy; phenyl $C_{1-4}$ alkoxy, such as benzyloxy, phenylethoxy, phenylpropoxy, etc., or substituted phenyl $C_{1-4}$ alkoxy; in terms of the substituted phenoxy or substituted phenyl $C_{1-4}$ alkoxy, the number of the substituted groups is one or more; the substituted groups are selected from the group consisting of $C_{1-4}$ alkyl, halo, cyano, and nitro, and the substituted groups may be the same or different, optionally, the groups are substituted at 2, 3, 4, 5 or 6-position of the benzene ring, for example 4-nitrobenzyloxyl, 2-chloro-4-nitrobenzyloxyl; amino, or benzylamino;

R1 is $C_{1-4}$ alkyl or hydrogen; the said $C_{1-4}$ alkyl is selected from methyl, ethyl, propyl, isopropyl, butyl, isobutyl, t-butyl; preferably, R1 is hydrogen or methyl.

The present invention provides the method of synthesizing the compound of Formula (I) mentioned above, after yielding the compound of Formula (IV), further including that if A and B are both $NHR_2$, the compound of Formula (IV) is heated and cyclized in or out of the presence of formamide or methanesulfonic acid to yield the compound of Formula (I); and with the proviso that when $R_2$ is not hydrogen, the compound of Formula (IV) undergoes deprotection of amino groups and then cyclization mentioned above to yield the compound of Formula (I);

when one of A and B is $NHR_2$ and the other is hydroxyl, the compound of Formula (IV) reacts in the presence of condensing agent (such as thionyl chloride, dicyclohexylcarbodiimide (DCC), phosphorus oxychloride, carbonyldiimidazole, etc.), to yield the compound of Formula (I); and with proviso that when $R_2$ is not hydrogen, the compound of Formula (IV) undergoes deprotection of amino groups and then cyclization mentioned above to yield the compound of Formula (I);

when one of A and B is $NHR_2$ and the other is $C_{1-10}$ alkoxy, aryloxy, or aryl $C_{1-4}$ alkoxy, the compound of Formula (IV) is cyclized in alkaline condition (such as in the presence of inorganic base, for example potassium carbonate, sodium carbonate, or organic base, for example potassium tert-butoxide or sodium methoxide, etc.), to yield the compound of Formula (I); and with the proviso that when $R_2$ is not hydrogen, the compound of Formula (IV) undergoes deprotection of amino groups and then cyclization mentioned above to yield the compound of Formula (I);

when A and B are both hydroxyl, the compound of Formula (IV) is cyclized in the presence of urea, or in the presence of trifluoroacetamide, 1-hydroxy benzotriazole (HOBT) and N-ethyl-N'-(3-dimethylaminopropyl) carbodiimide hydrochloride (EDCI), to yield the compound of Formula (I);

when A and B are both $C_{1-10}$ alkoxy, aryloxy or aryl $C_{1-4}$alkoxy, the compound of Formula (IV) is cyclized in the presence of alkali metal amide (such as lithium amide, sodium amide, potassamide, preferred sodium amide), to yield the compound of Formula (I);

when one of A and B is hydroxyl and the other is $C_{1-10}$ alkoxy, aryloxy or aryl $C_{1-4}$ alkoxy, the compound of Formula (IV) is firstly esterified, and then cyclized in the presence of alkali metal amide (such as lithium amide, sodium amide, potassamide, preferred sodium amide), to yield the compound of Formula (I); alternatively, the compound of Formula (IV) is firstly ester hydrolyzed, and then cyclized in the presence of urea, or in the presence of trifluoroacetamide, 1-hydroxy benzotriazole (HOBT) and N-ethyl-N'-(3-dimethylaminopropyl)carbodiimide hydrochloride (EDCI), to yield the compound of Formula (I); alternatively, the compound of Formula (IV) is firstly ammonolyzed and then reacts in the presence of condensing agent (such as thionyl chloride, dicyclohexylcarbodiimide (DCC), phosphorus oxychloride, carbonyldiimidazole, etc.), to yield the compound of Formula (I); alternatively, the compound of Formula (IV) is firstly acylated, converting its hydroxyl to amino, and then cyclized in alkaline condition (such as in the presence of inorganic base, for example potassium carbonate, sodium carbonate, etc., or organic base, for example potassium tert-butoxide or sodium methoxide, etc.), to yield the compound of Formula (I);

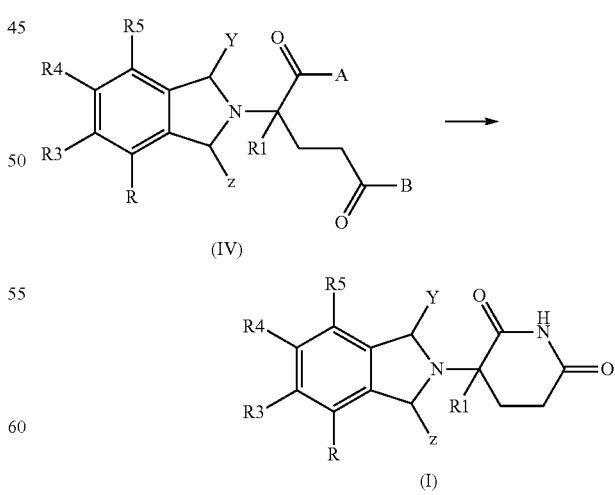

wherein, each substituted group in the Formula (IV) or (I) is defined as above.

Optionally, the above-mentioned method for synthesizing the compound of Formula (I) provided by the invention includes that, after yielding the compound of Formula (IV), when A and B are both $C_{1-10}$ alkoxy, aryloxy, or aryl $C_{1-4}$ alkoxy, the compound of Formula (IV) is ammonolyzed to yield the monoamide compound of Formula (IV'), and then the monoamide compound of Formula (IV') is cyclized in alkaline condition (such as in the presence of inorganic base, for example potassium carbonate, sodium carbonate, etc., or organic base, for example potassium tert-butoxide or sodium methoxide, etc.), to yield the compound of Formula (I); the monoamide compound of Formula (IV') may alternatively continue to be ammonolysed to yield eventually diamide of Formula (IV"), and then diamide of Formula (IV") is heated to be cyclized in or out of the presence of formamide or methanesulfonic acid to yield the compound of Formula (I);

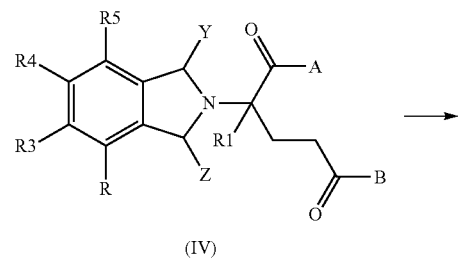

(IV)

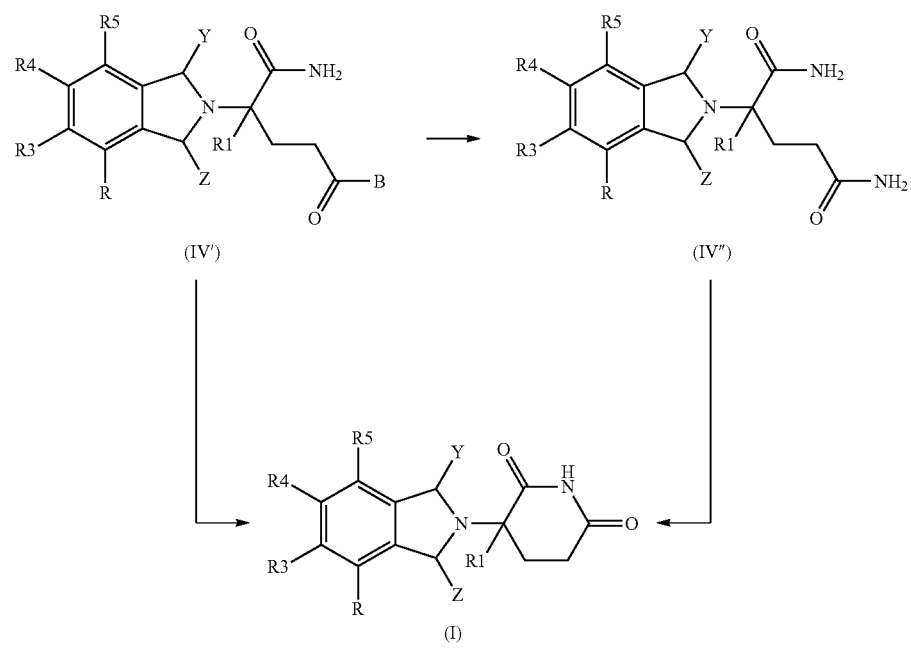

wherein, each substituted group in the Formula (IV), (IV'), (IV") and (I) is defined as above.

Optionally, the above-mentioned method for synthesizing the compound of Formula (I) provided by the invention, after yielding the compound of Formula (IV), when A and B are both $C_{1-10}$ alkoxy, aryloxy, or aryl$C_{1-4}$alkoxy further includes that the compound of Formula (IV) is hydrolyzed to yield the monoamide compound of Formula (V):

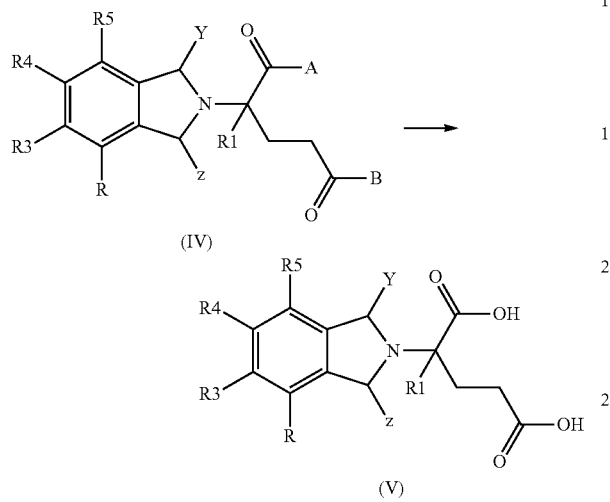

(IV)

(V)

wherein, each substituted group in the Formula (IV) and (V) is defined as above.

The above-mentioned method for synthesizing the compound of Formula (I) provided by the present invention, after yielding the compound of Formula (V), further includes that the compound of Formula (V) is cyclized (such as in the condition of acid anhydride and heating) to yield the compound of Formula (VI);

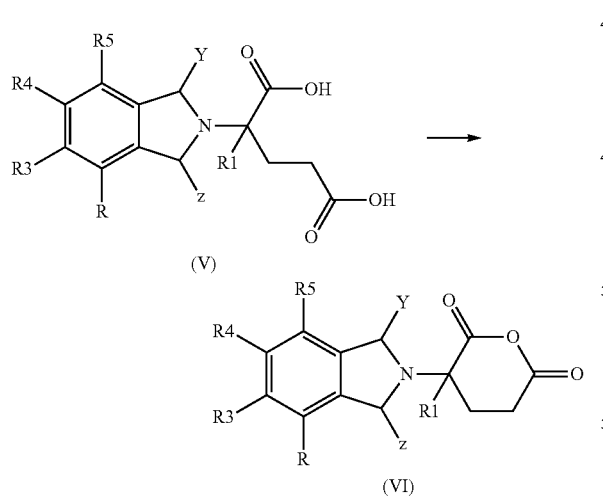

(V)

(VI)

wherein, each substituted group in the Formula (V) and (VI) is defined as above.

The above-mentioned method for synthesizing the compound of Formula (I) provided by the present invention, after yielding the compound of Formula (VI), further includes that the compound of Formula (VI) is ring-opening ammonolyzed to yield the compound of Formula (VII); then the compound of Formula (VII) reacts in the presence of condensing agent (such as thionylchloride, dicyclohexylcarbodiimide (DCC), phosphorus oxychloride, carbonyldiimidazole, etc.), to yield the compound of Formula (I):

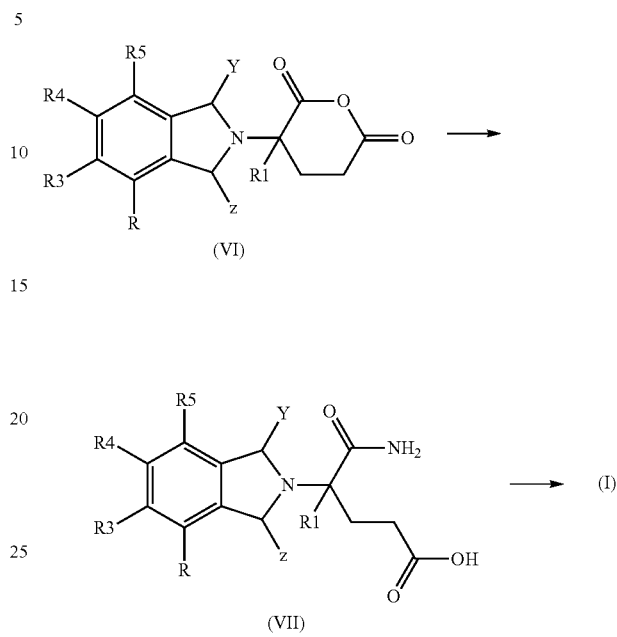

(VI)

(VII)

wherein, each substituted group in the Formula (VI) and (VII) is defined as above.

The present invention provided a novel method for synthesizing the compound of Formula (I), which includes the following steps:

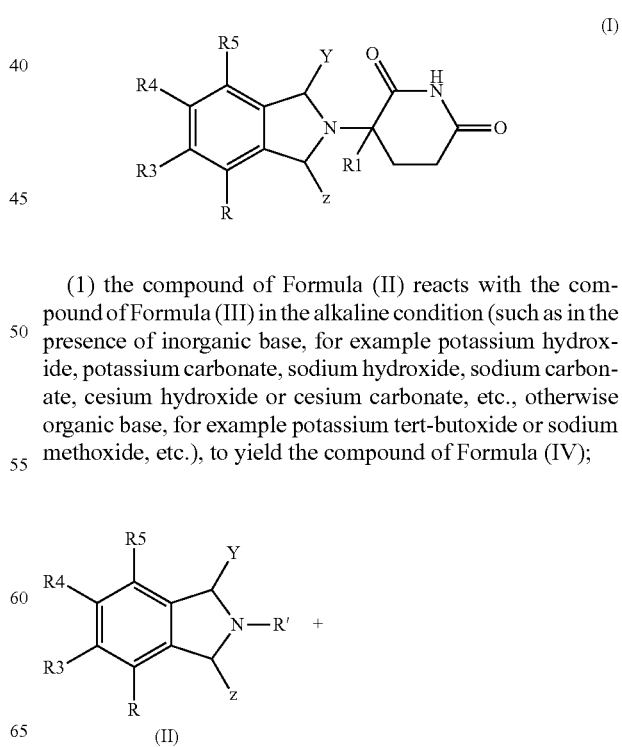

(I)

(1) the compound of Formula (II) reacts with the compound of Formula (III) in the alkaline condition (such as in the presence of inorganic base, for example potassium hydroxide, potassium carbonate, sodium hydroxide, sodium carbonate, cesium hydroxide or cesium carbonate, etc., otherwise organic base, for example potassium tert-butoxide or sodium methoxide, etc.), to yield the compound of Formula (IV);

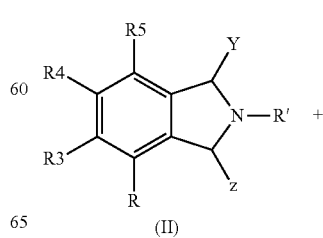

(II)

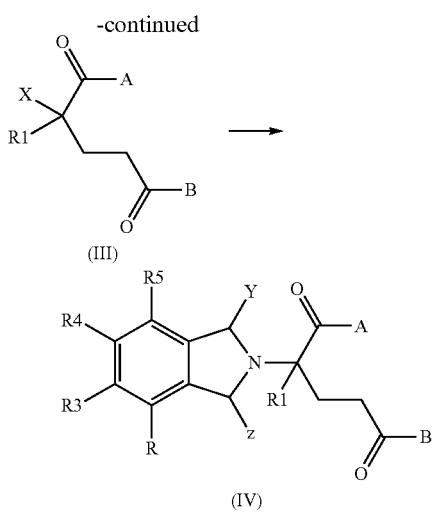

(III)

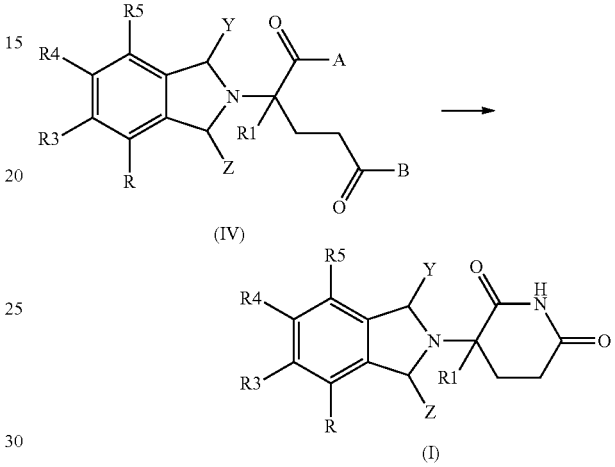

(IV)

(2) when A and B are both NHR$_2$, the compound of Formula (IV) is heated and cyclized in or out of the presence of formamide or methanesulfonic acid to yield the compound of Formula (I); and with the proviso that when R$_2$ is not hydrogen, the compound of Formula (IV) undergoes deprotection of amino groups and then cyclization mentioned above to yield the compound of Formula (I);

when one of A and B is NHR$_2$ and the other is hydroxyl, the compound of Formula (IV) reacts in the presence of condensing agent (such as thionyl chloride, dicyclohexylcarbodiimide (DCC), phosphorus oxychloride, carbonyldiimidazole, etc.), to yield the compound of Formula (I); and with the proviso that when R$_2$ is not hydrogen, the compound of Formula (IV) undergoes deprotection of amino groups and then cyclization mentioned above to yield the compound of Formula (I);

when one of A and B is NHR$_2$ and the other is C$_{1-10}$ alkoxy, aryloxy, or aryl C$_{1-4}$alkoxy, the compound of Formula (IV) is cyclized in alkaline condition (such as in the presence of inorganic base, for example potassium carbonate, sodium carbonate, etc., or organic base, for example potassium tert-butoxide or sodium methoxide, etc.), to yield the compound of Formula (I); and with the proviso that if R$_2$ is not hydrogen, the compound of Formula (IV) undergoes deprotection of amino groups and then cyclization mentioned above to yield the compound of Formula (I);

when A and B are both hydroxyl, the compound of Formula (IV) is cyclized in the presence of urea, or in the presence of trifluoroacetamide, 1-hydroxy benzotriazole (HOBT) and N-ethyl-N'-(3-dimethylaminopropyl)carbodiimide hydrochloride (EDCI), to yield the compound of Formula (I);

when A and B are both C$_{1-10}$ alkoxy, aryloxy or aryl C$_{1-4}$alkoxy, the compound of Formula (IV) is cyclized in the presence of alkali metal amide (such as lithium amide, sodium amide, potassamide, preferred sodium amide), to yield the compound of Formula (I);

when one of A and B is hydroxyl and the other is C$_{1-10}$ alkoxy, aryloxy or aryl C$_{1-4}$ alkoxy, the compound of Formula (IV) is firstly esterified, and then cyclized in the presence of alkali metal amide (such as lithium amide, sodium amide, potassamide, preferred sodium amide), to yield the compound of Formula (I); alternatively, the compound of Formula (IV) is firstly ester hydrolyzed, and then cyclized in the presence of urea, or in the presence of trifluoroacetamide, 1-hydroxybenzotriazole (HOBT) and N-ethyl-N'-(3-dimethylamino propyl)-carbodiimide hydrochloride (EDCI), to yield the compound of Formula (I); alternatively, the compound of Formula (IV) is firstly ammonolyzed and then reacts in the presence of condensing agent (such as thionyl chloride dicyclohexylcarbodiimide (DCC), phosphorus oxychloride, carbonyldiimidazole, etc.), to yield the compound of Formula (I); alternatively, the compound of Formula (IV) is firstly acylated, converting hydroxyl to amino, and then cyclized in alkaline condition (such as in the presence of inorganic base, for example potassium carbonate, sodium carbonate, etc., or organic base, for example potassium tert-butoxide or sodium methoxide, etc.), to yield the compound of Formula (I).

(IV)

(I)

wherein, each substituted group in the compounds of Formula from (I) to (IV) mentioned above is defined as:

one of R, R3, R4 and R5 is amino or protected amino (carbamates: such as carbobenzyloxy, t-butyloxycarbonyl, fluorenylmethoxycarbonyl, etc.; acyl amides: such as acetyl, phenylacetyl, phthalyl, etc.; azanes: such as allyl, etc.; sulfonyl and sulfinyl: such as phenylsulfonyl, p-toluenesulfonyl, phenylsulfiny, O-nitrophenylsulfinyl, etc.; referred to Greene T. W. and WuTs P. G. M. *Protective Groups in Organic Synthesis*: P494-; East China University Of Science And Technology Press), nitro or halo (for example F, Cl, Br or I), and the others are hydrogen, preferably, R3, R4 and R5 are hydrogen;

X is halo, such as: F, Cl, Br or I;

Y is =O or H;

Z is =O or H;

and with the proviso that Y and Z are both =O; or one of Y and Z is =O and the other is H;

R' is alkali metal ion or hydrogen, such as: H; Li$^+$; Na$^+$; K$^+$; Cs$^+$; or imine group (such as ethoxycarbonyl, etc.; referred to Greene T. W. and WuTs P. G. M. *Protective Groups in Organic Synthesis*: P494-, East China University Of Science And Technology Press, and referred to *Chemical Research and Application*: 2006, 18(11): 1349-1352), etc. preferably K$^+$ or Cs$^+$, and more preferably Cs$^+$;

A and B are each independently hydroxyl, C$_{1-10}$ alkoxy, aryloxy, aryl C$_{1-4}$ alkoxy or NHR$_2$ in which R$_2$ is hydrogen or amino protecting group (carbamates: such as carbobenzyloxy, t-butyloxycarbonyl, fluorenylmethoxycarbonyl, etc.; acyl amides: such as acetyl, phenylacetyl, phthalyl, etc.; azanes: such as allyl, etc.; sulfonyl and sulfinyl: such as phenylsulfonyl, p-toluenesulfonyl, phenylsulfiny, O-nitrophenylsulfinyl, etc.; referred to *Protective Groups in Organic Synthesis*: Greene T. W., WuTs P. G. M. East China University Of Science And Technology Press: P494-); preferably, A and B are each independently hydroxyl, methoxy, ethoxyl, propoxy, isopropoxy, butoxy, isobutoxy, t-butoxy, pentyloxy, hexyloxy, heptyloxy, octyloxy, nonyloxy, decyloxy; phenoxy or substituted phenoxy; phenyl C1-4 alkoxy, such as benzyloxy, phenylethoxy, phenylpropoxy, etc., or substituted phenyl $C_{1-4}$ alkoxy; in terms of the substituted phenoxy or substituted phenyl C1-4 alkoxy, the substituted groups are selected from the group consisting of $C_{1-4}$ alkyl, halo, cyano, nitro, and the substituted groups are one or more, which could be the same or different groups; optionally, the groups are substituted in 2, 3, 4, 5 or 6-position of the benzene ring, for example 4-nitrobenzyloxyl, 2-chloro-4-nitrobenzyloxyl; amino and benzylamino.

R1 is $C_{1-4}$ alkyl or hydrogen; the described $C_{1-4}$ alkyl is selected from methyl, ethyl, propyl, isopropyl, butyl, isobutyl, and t-butyl; preferably, R1 is hydrogen or methyl.

Optionally, in the above-mentioned method for synthesizing the compound of Formula (I) provided by the invention, the step (2) is: when A and B are both $C_{1-10}$ alkoxy, aryloxy, or aryl$C_{1-4}$alkoxy, the compound of Formula (IV) is ammonolyzed to yield the monoamide compound of Formula (IV'), and then the monoamide compound of Formula (IV') is cyclized in alkaline condition (such as in the presence of inorganic base, for example potassium carbonate, sodium carbonate, etc., or organic base, for example potassium tert-butoxide or sodium methoxide, etc.), to yield the compound of Formula (I); the monoamide compound of Formula (IV') may alternatively continue to be ammonolysed to yield eventually diamide of Formula (IV"), and then diamide of Formula (IV") is heated to be cyclized in or out of the presence of formamide or methanesulfonic acid, to yield the compound of Formula (I);

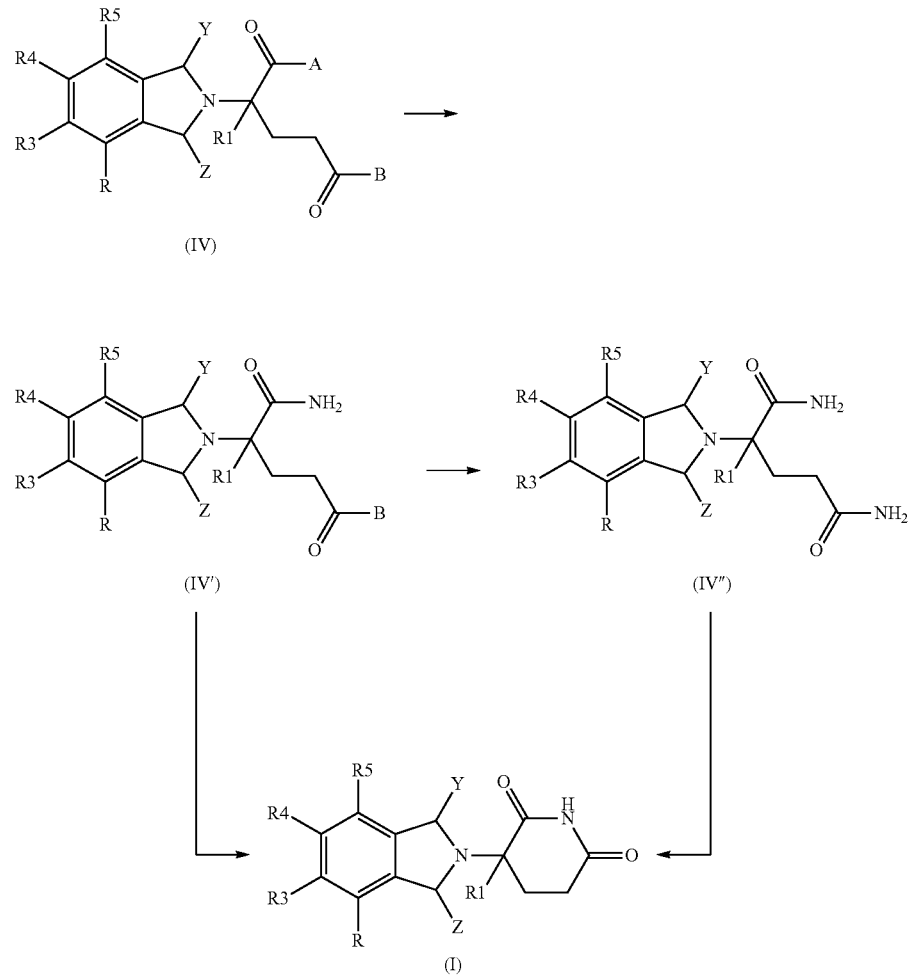

wherein, each other substituted group in the Formula (IV), (IV'), (IV") and (I) is defined as above.

Optionally, in the above-mentioned method for synthesizing the compound of Formula (I) provided by the invention, the step (2) is: when A and B are both $C_{1-10}$ alkoxy, aryloxy, or aryl$C_{1-4}$alkoxy the compound of Formula (IV) is hydrolyzed to yield the monoamide compound of Formula (V);

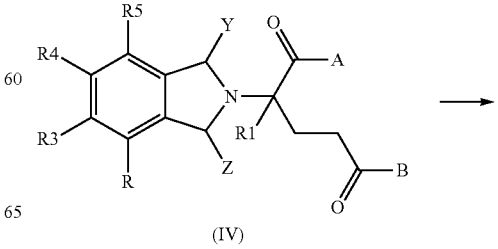

-continued

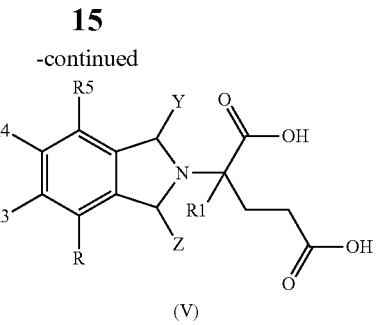

(V)

after yielding the compound of Formula (V), the compound of Formula (V) is further cyclized (such as in the condition of acid anhydride and heating) to yield the compound of Formula (VI);

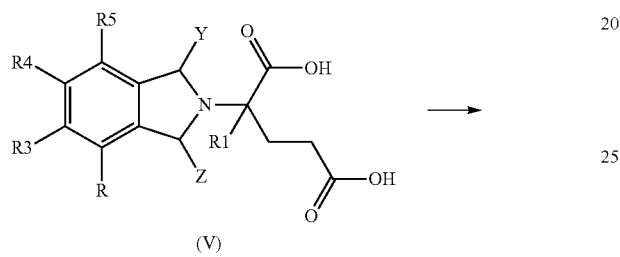

(VI)

after yielding the compound of Formula (VI), the compound of Formula (VI) is further ring-opening ammonolyzed to yield the compound of Formula (VII); then the compound of Formula (VII) reacts in the presence of condensing agent (such as thionylchloride, dicyclohexylcarbodiimide (DCC), phosphorus oxychloride, carbonyldiimidazole, etc.), to yield the compound of Formula (I):

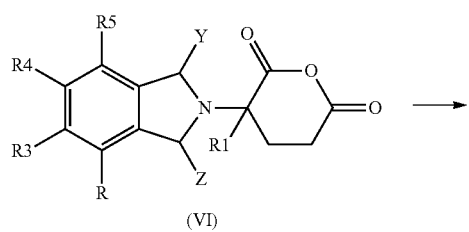

(VI)

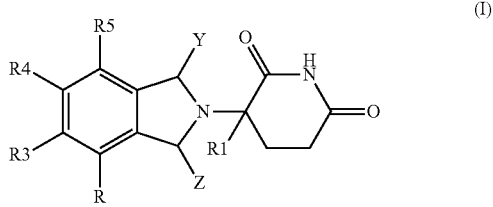

(VII) → (I)

wherein, each other substituted group in the Formula (IV), (V), (VI) and (VII) is defined as above.

More preferably, the present invention provides a method for preparing 3-(substituted dihydroisoindolinone-2-yl)-2,6-dioxopiperidine, i.e. the compound of Formula (I), including:

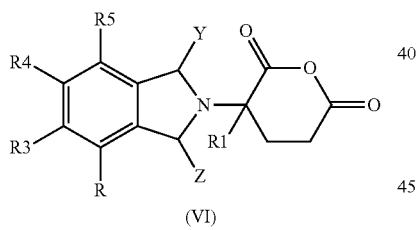

(I)

wherein: in the formula (I), substituted group R is amino, nitro or halo (such as F, Cl, Br or I); R3, R4 and R5 are all hydrogen;

Y is =O; Z is H;

R1 is hydrogen or methyl;

(1) the following compound of Formula (II) is stirred in the presence of potassium hydroxide, potassium carbonate, sodium hydroxide, sodium carbonate, cesium hydroxide or cesium carbonate for 5 minutes~6 hours; preferably, in the presence of potassium hydroxide, potassium carbonate, cesium hydroxide or cesium carbonate, and more preferably in the presence of cesium hydroxide or cesium carbonate; the reaction time is preferably 10 minutes~4 hours, and more preferably 20 minutes~4 hours; then the corresponding compound of Formula (III) is added into the reaction system to react with stirring, the reaction temperature is −20° C.~80° C.; the reaction temperature is preferably −20° C.~50° C., and more preferably 10° C.~30° C.; the reaction time is 1 hour~72 hours, preferably 8 hours~48 hours, and more preferably 12 hours~28 hours; the corresponding compound of Formula (IV) is yielded in the reaction.

in these conditions:

| sequence number | Compound of Formula (II) | Compound of Formula (III) | Compound of Formula (IV) |
|---|---|---|---|
| 1 | 4-amino isoindolin-1-one | dimethyl 2-bromoglutarate | dimethyl 2-(4-amino-1-oxoisoindolin-2-yl)glutarate |
| 2 | 4-nitro isoindolin-1-one | dimethyl 2-bromoglutarate | dimethyl 2-(4-nitro-1-oxoisoindolin-2-yl)glutarate |
| 3 | 4-chloro isoindolin-1-one | dimethyl 2-bromoglutarate | dimethyl 2-(4-chloro-1-oxoisoindolin-2-yl)glutarate |
| 4 | 4-nitro isoindolin-1-one | dimethyl 2-bromo-2-methylglutarate | dimethyl 2-methyl-2-(4-nitro-1-oxoisoindolin-2-yl)glutarate |

(2) the compound of Formula (IV) in step (1) is cyclized in the presence of alkali metal amide (such as lithium amide, sodium amide, potassamide, preferred sodium amide); the reaction temperature is −60° C.~80° C., preferably −40° C.~50° C., and more preferably −30° C.~20° C.; the reaction time is 30 minutes~24 hours, preferably 1 hour~12 hours, and more preferably 2 hours~8 hours; the corresponding compounds of Formula (I) are yielded in the reaction;

alternatively, the compound of Formula (IV) in step (1) is cyclized in the presence of urea; the reaction temperature is 50~250° C. preferably 100~200° C., and more preferably 130~160° C.; the reaction time is 30 minutes~24 hours, preferably 1 hour~12 hours, and more preferably 2 hours~8 hours; the corresponding compounds of Formula (I) are yielded in the reaction;

in these conditions:

| sequence number | Compound of Formula (IV) | conditions | Compound of Formula (I) |
|---|---|---|---|
| 1 | dimethyl 2-(4-amino-1-oxoisoindolin-2-yl)glutarate | NaNH₂ or KNH₂ | 3-(4-amino-1-oxoisoindolin-2-yl)piperidine-2,6-dione |

-continued

| sequence number | Compound of Formula (IV) | conditions | Compound of Formula (I) |
|---|---|---|---|
| 2 | 2-(4-amino-1-oxoisoindolin-2-yl)pentanedioic acid | NH₂CONH₂ | 3-(4-amino-1-oxoisoindolin-2-yl)piperidine-2,6-dione |
| 3 | dimethyl 2-(4-nitro-1-oxoisoindolin-2-yl)pentanedioate | NaNH₂ or KNH₂ | 3-(4-amino-1-oxoisoindolin-2-yl)piperidine-2,6-dione |
| 4 | 2-(4-nitro-1-oxoisoindolin-2-yl)pentanedioic acid | NH₂CONH₂ | 3-(4-nitro-1-oxoisoindolin-2-yl)piperidine-2,6-dione |
| 5 | dimethyl 2-(4-chloro-1-oxoisoindolin-2-yl)pentanedioate | NaNH₂ or KNH₂ | 3-(4-chloro-1-oxoisoindolin-2-yl)piperidine-2,6-dione |
| 6 | 2-(4-chloro-1-oxoisoindolin-2-yl)pentanedioic acid | NH₂CONH₂ | 3-(4-chloro-1-oxoisoindolin-2-yl)piperidine-2,6-dione |
| 7 | 2-methyl-2-(4-nitro-1-oxoisoindolin-2-yl)pentanedioic acid | NH₂CONH₂ | 3-methyl-3-(4-nitro-1-oxoisoindolin-2-yl)piperidine-2,6-dione | alternatively, the compound of Formula (IV) in step (1) is ammonolyzed in alkaline condition to yield the monoamide compounds of Formula (IV'); then the monoamide compound of Formula (IV') is cyclized in the condition of alkali such as potassium tert-butoxide, potassium carbonate etc. to yield the compound of Formula (I); alternatively the monoamide compound of Formula (IV') continues to be ammonolyzed to yield diamide compound of Formula (IV"), and then the compound of Formula (IV") is heated to be cyclized to yield the compound of Formula (I);

in particular, preferred ammonolysis conditions are: the compound of Formula (IV) is added into a single organic solvent or mixture of two or more organic solvents containing saturated ammonia such as ammonia water, ammonia/methanol, ammonia/tetrahydrofuran, ammonia/dioxane or ammonia/dimethylformamide; preferably ammonia/methanol or ammonia/tetrahydrofuran; the reaction temperature is between −20° C. and the refluxing temperature, preferably −10° C.~40° C., and more preferably 0° C.~20° C.; the reaction time for preparing the compound of Formula (IV') is 10 minutes~18 hours, preferably 2 hours~12 hours, more preferably 3 hours~8 hours; the synthesis time of the compound of Formula (IV") is 6 hours~72 hours, preferably 8 hours~32 hours, more preferably 10 hours~24 hours;

optional reaction conditions of cyclization of the compound of Formula (IV') are: in the presence of alkali, by cyclization the compound of Formula (I) is yielded. In particular, when metal organic base such as potassium tert-butoxide or sodium tert-butoxide is selected, reaction temperature is between −20° C. and the refluxing temperature, preferably −10° C.~50° C., and more preferably 0° C.~20° C.; reaction time is 10 minutes~48 hours, preferably 20 minutes~24 hours, more preferably 30 minutes~6 hours. When inorganic base such as potassium carbonate or sodium carbonate is selected, reaction solvent can be acetonitrile or tetrahydrofuran, and reaction temperature can be between 30° C. and the refluxing temperature;

in these condition:

optional reaction conditions of synthesis of the compound of formula (I) by cyclization of the compound of Formula (IV''') are: in or out of the presence of formamide or methanesulfonic acid, by heated cyclization the compound of Formula (I) is yielded. In particular, the optional reaction temperature is 0° C.~250° C., preferably 60° C.~200° C. and more preferably 120° C.~180° C.; the reaction time is 10 minutes~12 hours, preferably 1 hour~10 hours, more preferably 2 hours~8 hours;

in these conditions:

alternatively, the compound of Formula (IV) in the step (1) is hydrolyzed to yield the compound of Formula (V), and the reaction conditions in particular are: the compound of Formula (IV) is posed in a mixture system of organic solvent (the solvent is selected from acetonitrile, tetrahydrofuran, dioxane, methyl tert-butyl ether, dichloromethane, etc., preferably, a single solvent or mixture of two or more solvents of acetonitrile, tetrahydrofuran, dioxane) and water in any optional ratio; in the alkali system of potassium carbonate, sodium carbonate, sodium hydroxide, potassium hydroxide

| sequence number | Compound of Formula (IV) | Compound of Formula (IV''') | Compound of Formula (I) |
|---|---|---|---|
| 1 | | | |
| 2 | | | |
| 3 | | | |
| 4 | | | | or lithium hydroxide, at certain temperature, by stirred reaction the compound of Formula (V) is yielded, in which alkaline condition is preferably lithium hydroxide, sodium hydroxide, sodium carbonate or potassium carbonate, and more preferably potassium carbonate or sodium carbonate. To yield the compound of Formula (V), the reaction temperature can be between −20° C. and the refluxing temperature, preferably between room temperature and the refluxing temperature, and more preferably 30° C.~50° C.; the reaction time is 30 minutes~24 hours, preferably 8 hours~24 hours, more preferably 12 hours~18 hours;

in these conditions:

after that, the obtained compound of Formula (V) is cyclized to yield the compound of Formula (VI), and the specific reaction procedure is: in dry surrounding a mixture of the compound of Formula (V), acetic anhydride and catalytic amount of pyridine is stirred by heating up and then the reactant is concentrated to dryness to yield the compound of Formula (VI), wherein: to yield the compound of Formula (VI), the reaction temperature is between room temperature and 120° C., preferably between 40° C.~100° C. and more preferably 50° C.~80° C.; the reaction time, in particular, is 1 minute~12 hours, preferably 10 minutes~6 hours, more preferably 20 minutes~4 hours;

| sequence number | Formula | |
|---|---|---|
| | Compound of Formula (IV) | Compound of Formula (V) |
| 1 | [structure: 4-amino-isoindolinone with dimethyl glutarate substituent on N] | [structure: 4-amino-isoindolinone with glutaric acid substituent on N] |
| 2 | [structure: 4-nitro-isoindolinone with dimethyl glutarate substituent on N] | [structure: 4-nitro-isoindolinone with glutaric acid substituent on N] |
| 3 | [structure: 4-chloro-isoindolinone with dimethyl glutarate substituent on N] | [structure: 4-chloro-isoindolinone with glutaric acid substituent on N] |
| 4 | [structure: 4-nitro-isoindolinone with α-methyl dimethyl glutarate substituent on N] | [structure: 4-nitro-isoindolinone with α-methyl glutaric acid substituent on N] | in these conditions:
| sequence number | Compound of Formula (V) | Compound of Formula (VI) |
|---|---|---|
| 1 | 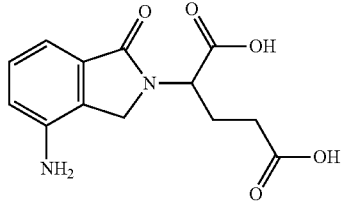 | 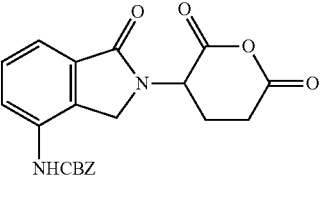 |
| 2 | 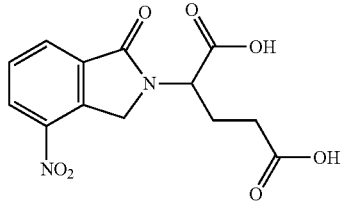 | 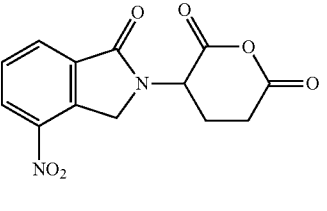 [SMILES: O=C1CCC(N2Cc3c(cccc3[N+](=O)[O-])C2=O)C(=O)O1] |
| 3 | 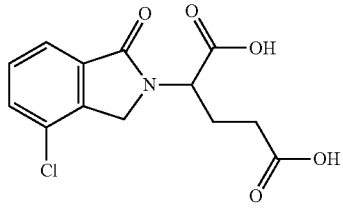 | 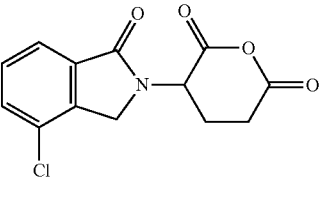 [SMILES: O=C1CCC(N2Cc3c(Cl)cccc3C2=O)C(=O)O1] |
| 4 | 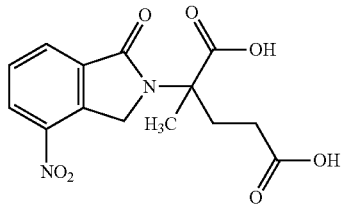 [SMILES: CC(CCC(=O)O)(C(=O)O)N1Cc2c(cccc2[N+](=O)[O-])C1=O] | 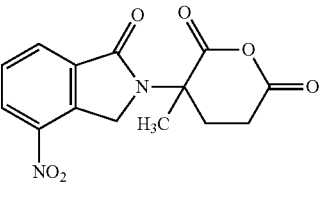 [SMILES: CC1(N2Cc3c(cccc3[N+](=O)[O-])C2=O)CCC(=O)OC1=O] | subsequently, the compound of Formula (VI) undergoes ring-opening ammonolysis to yield the compound of Formula (VII) which is then cyclized in the presence of condensing agent (such as thionyl chloride, dicyclohexylcarbodiimide (DCC), phosphorus oxychloride, carbonyldiimidazole, etc.), to yield the compound of Formula (I). In particular, the procedure of synthesis of the compound of Formula (VII) from the compound of Formula (VI) is: in dry surrounding, the compound of Formula (IV) is added into supersaturated solution of ammonia/methanol, ammonia/tetrahydrofuran, ammonia/dioxane or ammonia/dimethylformamide; the above ammonia organic solvent system can be a single organic solvent or mixture of two or more organic solvents of methanol, tetrahydrofuran, dioxane or dimethylformamide.

To yield the compound of Formula (VII), stirred reaction temperature is −40° C.~80° C., preferably −20° C.~50° C. and more preferably −10° C.~30° C.; the reaction time is 5 minutes~24 hours, preferably 30 minutes~12 hours, more preferably 1 hours~6 hours. In dry condition and in the reaction system of dimethylformamide, dimethylacetamide and halogenated hydrocarbon, thionyl chloride is added drop by drop into the compound of Formula (VII) to yield the compound of Formula (I), in which the reaction temperature is −40° C.~80° C., preferably −30° C.~40° C. and preferably −20° C.~20° C.; the reaction time is 10 minutes~24 hours, preferably 30 minutes~6 hours, more preferably 30 minutes~3 hours;

in these conditions:

| sequence number | Compound of Formula (VI) | Compound of Formula (VII) | Compound of Formula (I) |
|---|---|---|---|
| 1 | 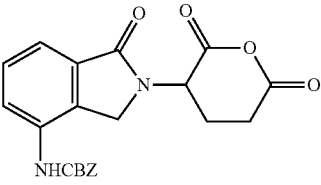 | 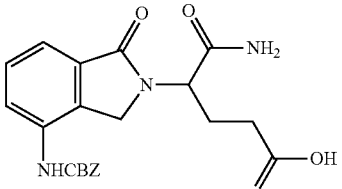 | 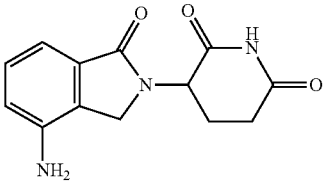 |
| 2 | 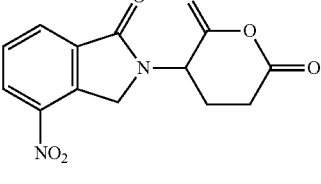 | 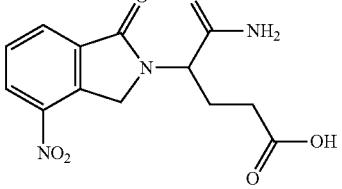 | 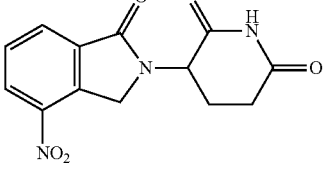 |
| 3 | 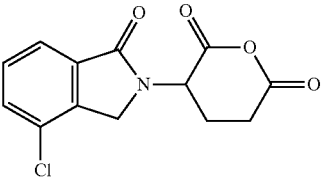 [SMILES: O=C1CCC(N2Cc3c(Cl)cccc3C2=O)C(=O)O1] | 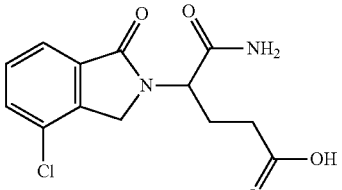 | 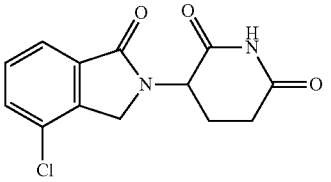 [SMILES: O=C1CCC(N2Cc3c(Cl)cccc3C2=O)C(=O)N1] |
| 4 | 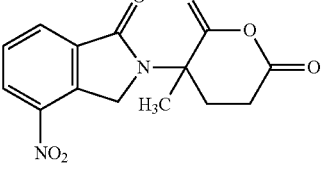 | 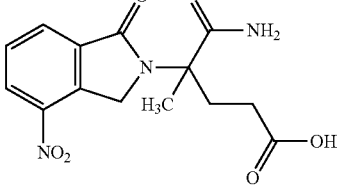 | 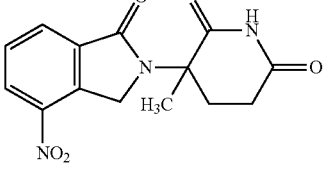 |

The reaction routes of the reaction process mentioned above are described in diagram A:
A:
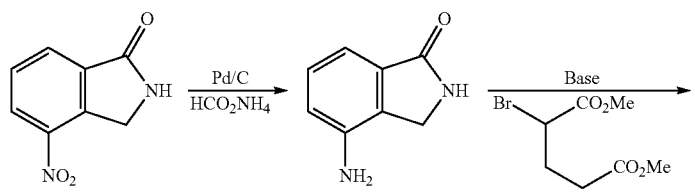
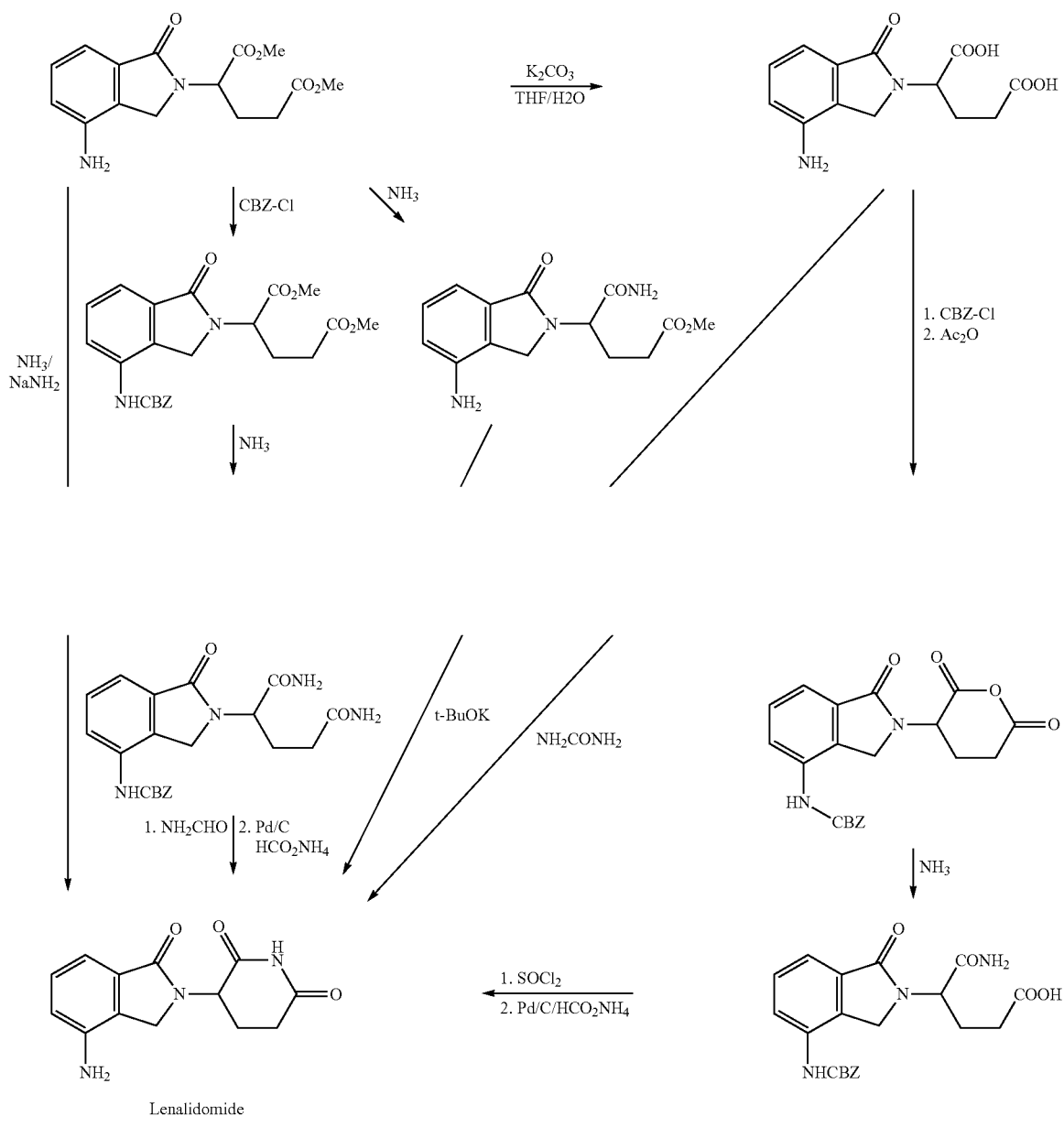
Lenalidomide The reaction routes of the reaction process mentioned above are described in diagram B:
B:
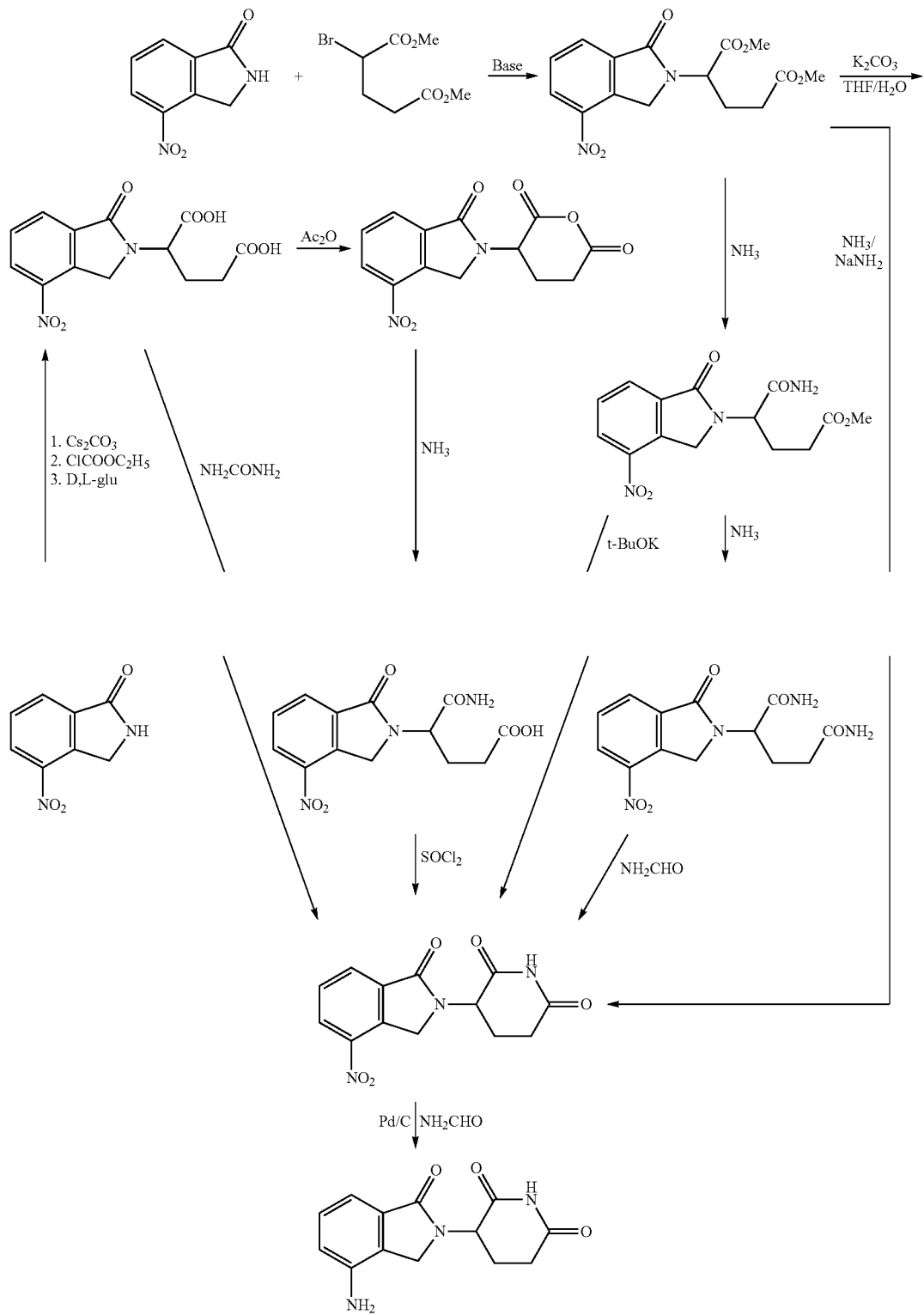

The reaction routes of the reaction process mentioned above are described in diagram C:
C:
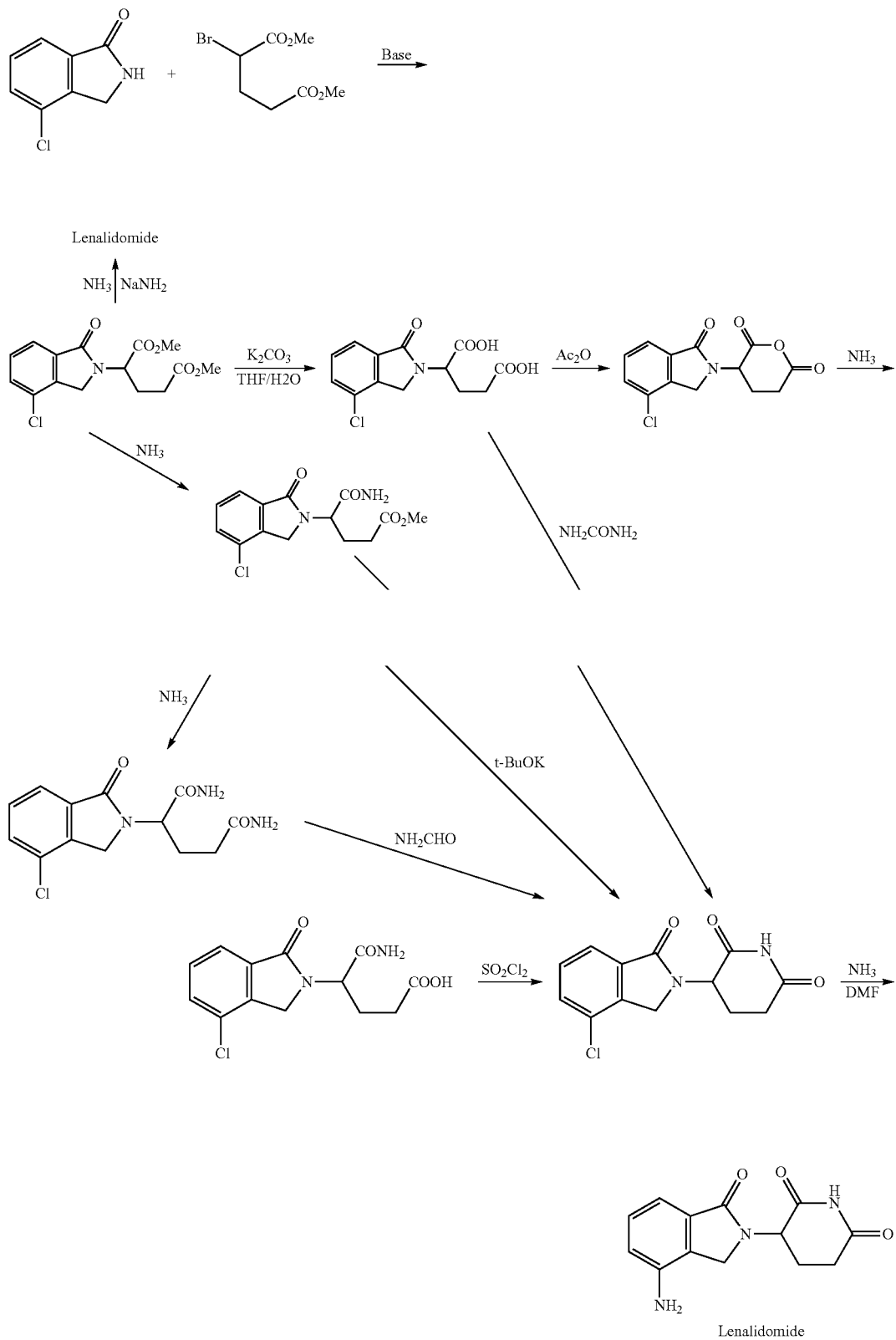

In another aspect of the invention, the following intermediate compounds of Formula (IV) are provided:

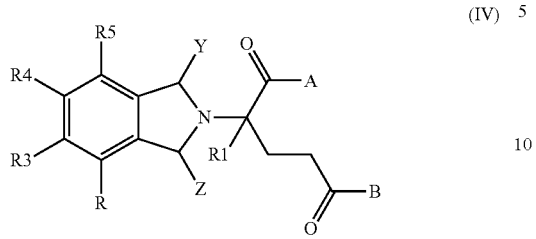

wherein:

One of R, R3, R4 and R5 is amino or protected amino (carbamates: such as carbobenzyloxy, t-butyloxycarbonyl, fluorenylmethoxycarbonyl, etc.; acyl amide: such as acetyl, phenylacetyl, phthalyl, etc.; azanes: such as allyl, etc.; sulfonyl and sulfinyl: such as phenylsulfonyl, p-toluenesulfonyl, phenylsulfinyl, O-nitrophenylsulfinyl, etc.; referred to T. W. and WuTs P. G. M. *Protective Groups in Organic Synthesis*: P494-; East China University Of Science And Technology Press), nitro or halo (for example F, Cl, Br or I), and the others are hydrogen. preferably, R3, R4 and R5 are hydrogen;

X is halo, such as: F, Cl, Br or I;

Y is =O or H;

Z is =O or H;

and with the proviso that Y and Z are both =O; or one of Y and Z is =O and the other of Y and Z is H;

A and B are each independently hydroxyl, $C_{1-10}$ alkoxy, aryloxy, aryl $C_{1-4}$ alkoxy or $NHR_2$, in which $R_2$ is hydrogen or amino protecting group (carbamates: such as carbobenzyloxy, t-butyloxycarbonyl, fluorenylmethoxycarbonyl, etc.; acyl amides: such as acetyl, phenylacetyl, phthalyl, etc.; azanes: such as allyl, etc.; sulfonyl and sulfinyl: such as phenylsulfonyl, p-toluenesulfonyl, phenylsulfinyl, O-nitrophenylsulfinyl, etc.; referred to *Protective Groups in Organic Synthesis*: Greene T. W., WuTs P. G. M. East China University Of Science And Technology Press: P494-); preferably, A and B are each independently hydroxyl, methoxy, ethoxyl, propoxy, isopropoxy, butoxy, isobutoxy, t-butoxy, pentyloxy, hexyloxy, heptyloxy, octyloxy, nonyloxy, decyloxy; phenoxy or substituted phenoxy; phenyl C1-4 alkoxy, such as benzyloxy, phenylethoxy, phenylpropoxy, etc., or substituted phenyl C1-4 alkoxy; in terms of the substituted phenoxy or substituted phenyl C1-4 alkoxy, the substituted groups are selected from the group consisting of $C_{1-4}$ alkyl, halo, cyano, nitro, and the substituted groups are one or more, which could be the same or different groups; optionally, the groups are substituted in 2, 3, 4, 5 or 6-position of the benzene ring, for example 4-nitrobenzyloxyl, 2-chlorine-4-nitrobenzyloxyl; amino and benzylamino;

R1 is $C_{1-4}$ alkyl or hydrogen; the described $C_{1-4}$ alkyl is selected from methyl, ethyl, propyl, isopropyl, butyl, isobutyl, t-butyl; preferably, R1 is hydrogen or methyl;

and with proviso that the following compounds are not included: when R is nitro, A and B are both methoxy, benzyloxy, hydroxyl or amino; when R is nitro, A is methoxy and B is amino; when R is amino, A and B are both ethoxyl; when R is nitro, A is amino and B is alkoxide.

Preferably, the present invention provides the compounds of Formula (IV'):

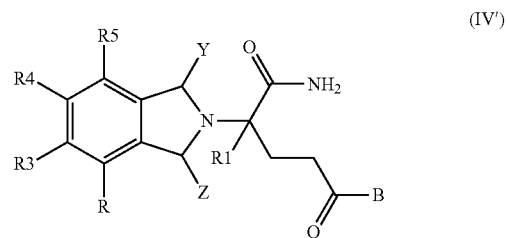

the definitions of the substituted groups in the compounds of Formula (IV') are identical to that in the compounds of Formula (IV); more preferably, one of Y and Z is =O, and the other is H.

Preferably, the present invention provides the compounds of Formula (IV"):

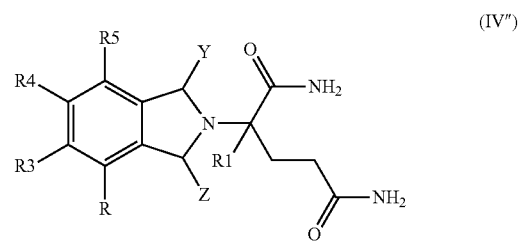

the definitions of the substituted groups in the compounds of Formula (IV") are identical to that in the compounds of Formula (IV); more preferably, one of Y and Z is =O, and the other is H.

Preferably, the present invention provides the compound of Formula (V):

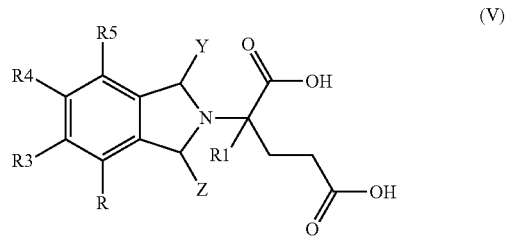

wherein: the definitions of the substituted groups in the compound of Formula (V) are identical to that in the compound of Formula (IV); more preferably, one of Y and Z is =O, and the other is H; and with the proviso that the following compounds are not included: when R is amino or nitro, R1, R3, R4 and R5 are all hydrogen, and Y is =O, and Z is =O or H.

Preferably, the present invention provides the compounds of Formula (VI):

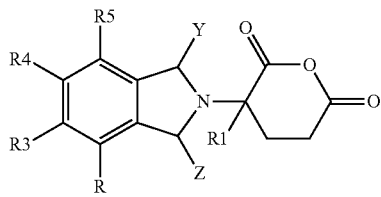
(VI)

wherein: the definitions of the substituted groups in the compounds of Formula (VI) are identical to that in the compounds of Formula (IV); more preferably, one of Y and Z is =O, and the other is H; and with the proviso that the following compounds are not included: when R is nitro, R1, R3, R4 and R5 are all hydrogen, and Y is =O, and Z is =O.

Preferably, the present invention provides the compounds of Formula (VII):

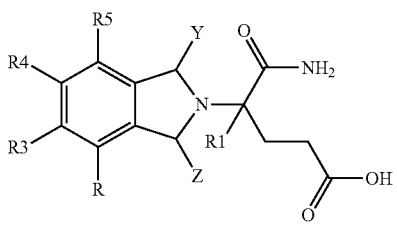
(VII)

wherein: the definitions of the substituted groups in the compounds of Formula (VII) are identical to that in the compounds of Formula (IV); more preferably, one of Y and Z is =O, and the other is H; and with the proviso that the following compounds are not included: when R is amino or nitro, R1, R3, R4 and R5 are all hydrogen, Y is =O, and Z is =O or H.

Further preferably, the present invention provides the compounds of following formula:

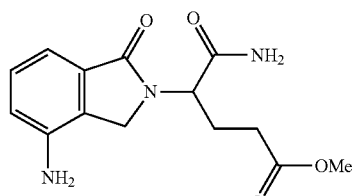

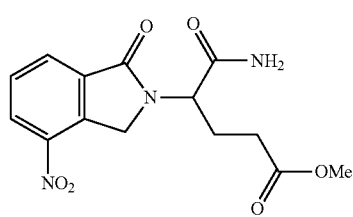 [SMILES: COC(=O)CCC(C(N)=O)N1Cc2c(cccc2[N+](=O)[O-])C1=O]

-continued

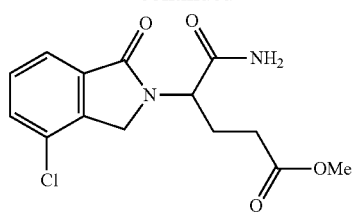 [SMILES: COC(=O)CCC(C(N)=O)N1Cc2c(Cl)cccc2C1=O]

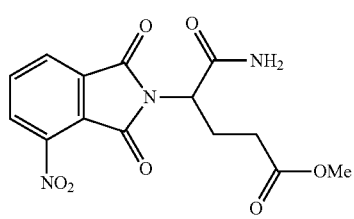

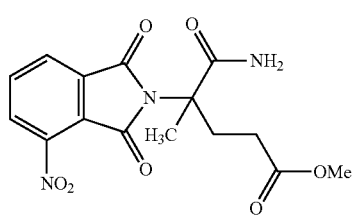

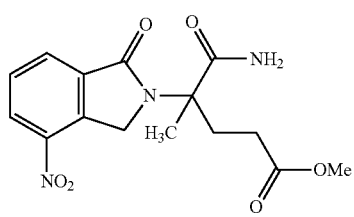 [SMILES: COC(=O)CCC(C)(C(N)=O)N1Cc2c(cccc2[N+](=O)[O-])C1=O]

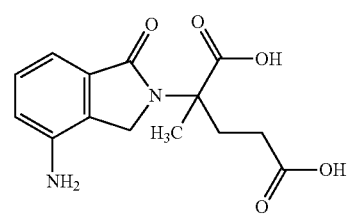

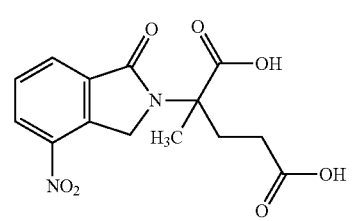 [SMILES: CC(CCC(=O)O)(C(=O)O)N1Cc2c(cccc2[N+](=O)[O-])C1=O]

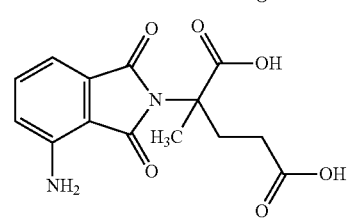

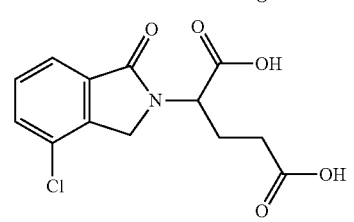

-continued

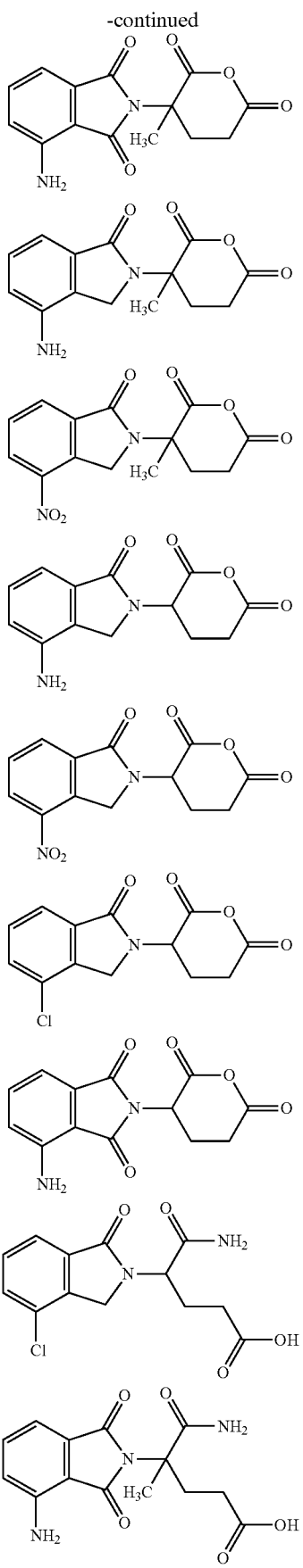

-continued

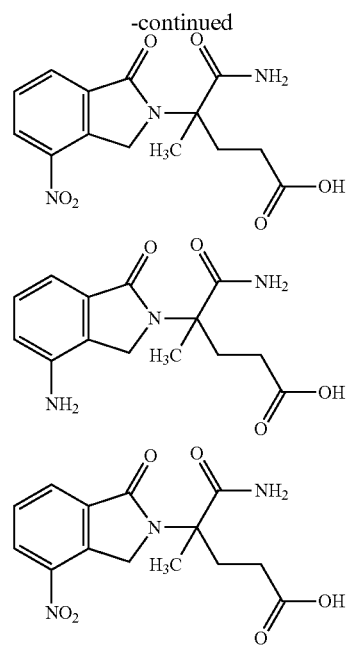

By comparison with the existing synthesis routes, the present invention has the following advantages:

1. The Raw Materials Used in the Present Invention are Accessible, Whereas the Raw Materials Used in Original R&D Corporation's Route are Commercially Unavailable Internally:

Initial materials: α-aminoglutarimide hydrochloride is commercially unavailable internally. It is synthesized from N-benzyloxycarbony-L-glutamine, which reacts with N,N'-carbonyldiimidazole in THF refluxing to yield N-benzyloxy-carbony-aminoglutarimide. After that amino protection group is removed and α-aminoglutarimide hydrochloride is yielded by hydrogenation under certain pressure catalyzed with Pd/C.

Key materials in reaction: methyl 2-bromomethyl-3-nitrobenzoate is synthesized from 2-methyl-3-nitrobenzoate, which is brominated by refluxing over 24 h in the presence of lethal carbon tetrachloride and in the condition of ultraviolet light photocatalysis under mercury lamp. Photocatalytic reaction has low yield and the difficulty in mass production, as well as the difficulty in labour protection against ultraviolet light emitted by the catalytic light source—mercury lamp.

2. Comparison of Time Length and Degree of Difficulty of Reaction, Yield Purity, as Well as Degree of Extraction and Purification:

In both the US Patent application US2006052609A1 and the Chinese Patent application CN97180299.8, the reaction product was purified by column chromatography at least twice or more, which made industrial operation complicated and made it difficult to industrial scale-up production.

In both the US Patent application US2006052609A1 and the Chinese Patent application CN97180299.8, pressurized hydrogenation was utilized twice. In the present invention, only Pd/C and ammonium formate are used in deprotection reduction, which is of high security and mild conditions. By comparison with hydrogenation under certain pressure, hydrogenation under atmospheric pressure is of less risk, leading to enhanced production security.

When N-benzyloxycarbony-L-glutamine, as initial material, reacted with N,N'-carbonyldiimidazole in THF refluxing for 24 h to yield N-benzyloxycarbony-aminoglutarimide, low purity of yield results from long reactive time and high temperature.

3. Comparison of Yield in Each Procedure and Total Yield:

The total yield was lower than 20% and 18% respectively reported in the US Patent application US2006052609A1 and the Chinese Patent application.

In the present invention, the total yield of 3-(4-amino-1-oxo-1,3-dihydro-2H-isoindol-2-yl)-2,6-dioxopiperidine synthesized from the original raw material, 4-nitro-2,3-dihydro-1H-isoindol-1-one and α-bromodimethyl glutarate, averages from 35% to 40%, due to the short reaction routes and simple methods.

4. Toxicity of Solvent and its Influence on Environment:

In the US Patent application US2006052609A1 and the Chinese Patent application, carbon tetrachloride was reported to be reaction solvent used for refluxing, which did extreme harm to environment and made innocent treatment and labor protection difficult.

In the present invention, derivatives of benzene or carbon tetrachloride are unavailable to be as reaction solvent, which is relatively eco-friendly.

DESCRIPTION OF EMBODIMENTS

The following examples will serve to further elaborate the present invention seeing the above routes A, B and C, which shouldn't be understood as a limitation in the scope of this invention by the person skilled in the art. Any modification or improvement based on the instruction well known in the art should be in the scope of this invention, without departing from the spirit and scope of the present invention.

Example 1

The synthesis of
4-nitro-2,3-dihydro-1H-isoindol-1-one

A mixture of methyl 2-bromomethyl-3-nitrobenzoate (20 g) and methanol (200 ml) was stirred under ammonia gas for 30 min at room temperature, and was kept in heat preservation for 2 hours. Crystal grew in an ice bath for 2 hours, and then filtered, and dried to give 11.7 g of light yellow crystal. yield: 90%. mp: 235.4~236.7° C.

$^1$H-NMR: (300 MHz, DMSO-$d_6$) δ: 4.78 (s, 2H), 7.79 (t, 1H), 8.10 (d, 1H), 8.41 (d, 1H), 8.90 (S, 1H).

$^1$H-NMR: (300 MHz, DMSO-$d_6$/$D_2O$) δ: 4.76 (s, 2H), 7.77 (t, 1H), 8.08 (d, 1H), 8.39 (d, 1H).

FAB(M+1): 179

Element analysis:
theoretical data: C, 53.94%; H, 3.39%; N, 15.72%
measured data: C, 54.08%; H, 3.49%; N, 15.81%
Test condition of HPLC:
type and specification of column: phenomenex Luna 5u C18
250 mm×4.6 mm; velocity: 1.0 ml/min; λ=230 nm
mobile phase: acetonitrile/0.1% phosphate=30/70
appearance time of target yield: 5.810 minutes
purity of target yield: 99.59%

Example 2

The synthesis of
4-amino-2,3-dihydro-1H-isoindol-1-one

A mixture of 4-nitro-2,3-dihydro-1H-isoindol-1-one (20 g), ammonium formate (35 g) and 7.5% Pd/C (0.6 g) in methanol (60 ml) was stirred for 2 hours by heating up to 35° C. Pd/C was filtered and the filtrate concentrated under reduced pressure. The residue was recrystallized from water to give 15.3 g of light yellow solid. yield: 92%. mp: 195.6-197° C.

$^1$H-NMR: (300 MHz, DMSO-$d_6$) δ: 4.31 (s, 2H), 6.76 (d, 1H), 7.14 (t, 1H), 6.86 (d, 1H), 5.30 (s, 2H), 8.26 (s, 1H)

$^1$H-NMR: (300 MHz, DMSO-$d_6$/$D_2O$) δ: 4.14 (s, 2H), 6.79 (d, 1H), 6.93 (d, 1H), 7.16 (t, 1H)

FAB(M+1): 149

Element analysis: theoretical data: C, 64.85%; H, 5.44%; N, 18.91%
measured data: C, 64.96%; H, 5.61%; N, 19.02%
Test condition of HPLC:
type and specification of column: phenomenex Luna 5u C18
250 mm×4.6 mm; velocity: 1.0 ml/min; λ=230 nm
mobile phase: acetonitrile/0.1% phosphate=15/85 or acetonitrile/0.01M ammonium acetate=10/90
appearance time of target yield: 3.580 minutes; 4.790 minutes purity of target yield: 99.66%

Example 3

The Synthesis of α-bromodimethyl glutarate

In a dry reaction flask, thionyl chloride 36 ml was added into a stirred mixture of glutaric acid (30 g) and chloroform (90 ml) under reflux for 2 hours, and then bromine (36 g) was added under reflux for over 16 hours. The reaction mixture was cooled, into which methanol (75 ml) was then added by droplet in an ice bath and stirred in heat preservation for 2 hours. The resulting mixture was washed with 5% sodium bisulfate (150 ml), saturated sodium bicarbonate (150 ml) and saturated sodium chloride (150 ml) one by one. The organic layer was dried with anhydrous sodium sulfate and after that sodium sulfate was removed by filter. The filtrate was concentrated to dryness and distilled under reduced pressure, to collect the fraction at 110-115V/5 mmHg. The target yield is colorless liquid. weight: 41.3 g. yield: 76%.

FAB(M+1): 240
Test condition of HPLC:
type and specification of column: phenomenex Luna 5u C18
250 mm×4.6 mm; velocity: 1.0 ml/min; λ=230 nm
mobile phase: acetonitrile/0.1% phosphate=50/50
appearance time of target yield: 7.750 minutes
purity of target yield: 96.64%

Example 4

The synthesis of dimethyl 3-(4-amino-1,3-dihydro-1-oxo-2H-isoindol-2-yl)-glutarate A mixture of 4-amino-2,3-dihydro-1H-isoindol-1-one (5 g), N-methylpyrrolidone (25 ml), cesium carbonate (11 g) and α-bromodimethyl glutarate (9.7 g) was stirred under nitrogen at room temperature over night. After adding water (75 ml) and methylene chloride (50 ml), remove the aqueous phase and the organic phase was extracted with 2 mol/L hydrochloric acid. The aqueous hydrochloric acid solution was mixed with methylene chloride (100 ml) and phases separated at pH7 adjusted by addition of $Na_2CO_3$. The organic phase was dried over anhydrous sodium sulfate and concentrated under reduced pressure to give a yellow ticking substance (7.2 g) which could be used in next reaction without further purification. yield: 70%

¹H-NMR: (300 MHz, DMSO-d₆) δ: 2.19 (m, 2H), 2.35 (t, 2H), 3.52 (s, 3H), 3.66 (s, 3H), 4.23 (s, 2H), 4.90 (m, 1H), 5.38 (s, 2H), 6.79 (d, 1H), 6.89 (d, 1H), 7.17 (t, 1H).
¹H-NMR: (300 MHz, DMSO-d₆/D₂O) δ: 2.10 (m, 2H), 2.33 (t, 2H), 3.53 (s, 3H), 3.66 (s, 3H), 4.22 (s, 2H), 4.90 (m, 1H), 5.38 (s, 2H), 6.80 (d, 1H), 6.89 (d, 1H), 7.17 (t, 1H).
FAB(M+1): 307
Element analysis: theoretical data: C, 58.82%; H, 5.92%; N, 9.15%
measured data: C, 58.74%; H, 6.06%; N, 9.06%
Test condition of HPLC:
type and specification of column: phenomenex Luna 5u C18
250 mm×4.6 mm; velocity: 1.0 ml/min; λ=230 nm
mobile phase: acetonitrile/0.1% phosphate=30/70
appearance time of target yield: 7.620 minutes
purity of target yield: 92.1%
With the similar methods, the compounds in the following table are obtained:

(690 mg) into liquid ammonia (−40° C., 300 ml) and then adding catalytic amount of ferric nitrate). The solution of dimethyl 3-(4-amino-1,3-dihydro-1-oxo-2H-isoindol-2-yl)-glutarate (3 g, 10 mmol) in anhydrous tetrahydrofuran (100 ml) was added by droplet with the temperature maintaining at −40° C. and the mixture was stirred in heat preservation for 3 hours. ammonium chloride (5 g) (ammonia spillover is allowed) and water (300 ml) were added and the resulting mixture was filtered. The crude was recrystallized from isopropanol (15 ml) to give target yield (1.22 g).
Yield 48%. mp: 251.5° C.~252.5° C.
¹H-NMR: (500 MHz, DMSO-d₆) δ: 2.02~2.04 (m, 1H), 2.27~2.34 (m, 1H), 2.60~2.63 (m, 1H), 2.88~2.95 (m, 1H), 4.16 (dd, 2H), 5.10 (dd, 2H), 6.80 (d, 1H), 6.92 (d, 1H), 7.19 (t, 1H), 10.19 (s, 1H)
FAB(M+1): 260
Element analysis: theoretical data: C, 60.22%; H, 5.05%; N, 16.21%
measured data: C, 60.14%; H, 5.16%; N, 16.30%

| | | Formula | | |
|---|---|---|---|---|
| sequence number | original raw material | starting material | target yield | yield/purity (HPLC by normalization) |
| 1 | [4-nitro-isoindolin-1-one structure] | [dimethyl 2-bromoglutarate structure] | [dimethyl 2-(4-nitro-1-oxoisoindolin-2-yl)glutarate structure] | yield: 68.3% purity: 93.5% |
| 2 | [4-chloro-isoindolin-1-one structure] | [dimethyl 2-bromoglutarate structure] | [dimethyl 2-(4-chloro-1-oxoisoindolin-2-yl)glutarate structure] | yield: 73.7% purity: 91.4% |
| 3 | [4-nitro-isoindolin-1-one structure] | [dimethyl 2-bromo-2-methylglutarate structure] | [dimethyl 2-methyl-2-(4-nitro-1-oxoisoindolin-2-yl)glutarate structure] | yield: 59.3% purity: 89.1% |

Example 5

The synthesis of 3-(4-amino-1-oxo-1,3-dihydro-2H-isoindol-2-yl)-2,6-dioxopiperidine Under nitrogen in dry reaction flask was added sodium amide (30 mmol 1.17 g) (obtained by adding metallic sodium Test condition of HPLC:
type and specification of column: phenomenex Luna 5u C18
250 mm×4.6 mm; velocity: 1.0 ml/min; λ=230 nm
mobile phase: acetonitrile/0.1% phosphate=10/90
appearance time of target yield: 11.81 minutes
purity of target yield: 99.29%

With the similar methods, the compounds in the following table are obtained:

| sequence number | starting material | target yield | yield/purity (HPLC by normalization) |
|---|---|---|---|
| 1 | isoindolinone-NO2 with dimethyl glutarate diester | isoindolinone-NO2 with glutarimide | yield: 53% purity: 93.23% |
| 2 | isoindolinone-Cl with dimethyl glutarate diester | isoindolinone-NH2 with glutarimide | yield: 39.7% purity: 94.77% |

Example 6

The synthesis of methyl N-[4-amin-1-oxo-1,3-dihydro-2H-isoindol-2-yl]-glutaminate A mixture of dimethyl 3-(4-amino-1,3-dihydro-1-oxo-2H-isoindol-2-yl)-glutarate (30.6 g), saturated dioxane/ammonia solution (150 ml) and lipase (14 g) was stirred at 20° C. for 3~5 hours. The reaction mixture concentrated by reduced pressure at room temperature to remove ammonia and then concentrated under reduced pressure to dryness. The concentrate was stirred with methyl tert-butyl ether (100 ml) and then white crystal was precipitated. After filter the residue was dried under vacuum at room temperature to give 21.4 g of target yield as a white crystal. yield: 73%. mp: 103-106° C.

$^1$H-NMR: (300 MHz, DMSO-$d_6$) δ: 4.17 (d, 1H), 4.40 (d, 1H), 5.43 (s, 2H), 6.76 (d, 1H), 7.17 (t, 1H), 6.87 (d, 1H), 4.73 (m, 1H), 1.91 (m, 2H), 2.18 (t, 2H), 3.51 (s, 3H), 7.13 (s, 1H), 7.55 (s, 1H).

$^1$H-NMR: (300 MHz, DMSO-$d_6$/$D_2O$) δ: 4.17 (d, 1H), 4.40 (d, 1H), 6.76 (d, 1H), 7.17 (t, 1H), 6.87 (d, 1H), 4.73 (m, 1H), 1.91 (m, 2H), 2.18 (t, 2H), 3.51 (s, 3H).

FAB(M+1): 292

Test condition of HPLC:

type and specification of column: phenomenex Luna 5u C18

250 mm×4.6 mm; velocity: 1.0 ml/min; λ=230 nm mobile phase: acetonitrile/0.1% phosphate=10/90 appearance time of target yield: 19.900 minutes purity of target yield: 98.3%

With the similar methods, the compounds in the following table are obtained:

| sequence number | starting material | target yield | yield/purity (HPLC by normalization) |
|---|---|---|---|
| 1 | isoindolinone-NO2 with dimethyl glutarate diester | isoindolinone-NO2 with glutamide (NH2) monoester | yield: 72% purity: 97.96% |
| 2 | isoindolinone-Cl with dimethyl glutarate diester | isoindolinone-Cl with glutamide (NH2) monoester | yield: 75.1% purity: 97.55% |

| sequence number | starting material | target yield | yield/purity (HPLC by normalization) |
|---|---|---|---|
| 3 | [structure: methyl 2-(4-nitro-1-oxoisoindolin-2-yl)-2-methyl glutarate dimethyl ester] | [structure: corresponding amide with NH2] | yield: 64.1% purity: 96.74% |

Example 7

The synthesis 3-(4-amino-1,3-dihydro-1-oxo-2H-isoindol-2-yl)-2,6-dioxopiperidine A mixture of methyl N-[4-amin-1-oxo-1,3-dihydro-2-hydro-isoindol-2-yl]-glutaminate (20 g) in acetonitrile (300 ml) was stirred with potassium carbonate (9.4 g) under reflux for 5 hours. The reaction mixture was concentrated to remove acetonitrile and was stirred with ethyl acetate (100 ml) and water (50 ml). After filter, recrystallization from isopropanol gave a light yellow solid (14.9 g). yield: 84%. mp: 250.5-251.7° C.

$^1$H-NMR: (300 MHz, DMSO-d$_6$) δ: 2.03~2.06 (m, 1H), 2.26~2.34 (m, 1H), 2.59~2.63 (m, 1H), 2.85~2.92 (m, 1H), 4.15 (dd, 2H), 5.09 (dd, 2H), 6.81 (d, 1H), 6.92 (d, 1H), 7.20 (t, 1H), 10.18 (s, 1H).

FAB(M+1): 260

Element analysis: theoretical data: C, 60.22%; H, 5.05%; N, 16.21% measured data: C, 60.12%; H, 5.17%; N, 16.29%

Test condition of HPLC:

type and specification of column: phenomenex Luna 5u C18

250 mm×4.6 mm; velocity: 1.0 ml/min; λ=230 nm mobile phase: acetonitrile/0.1% phosphate=10/90 appearance time of target yield: 11.73 minutes purity of target yield: 99.61%

With the similar methods, the compounds in the following table are obtained:

| Formula sequence number | starting material | target yield | yield/purity (HPLC by normalization) |
|---|---|---|---|
| 1 | [structure: 4-Cl isoindolinone glutamine amide methyl ester] | [structure: 3-(4-chloro-1-oxoisoindolin-2-yl)piperidine-2,6-dione] | yield: 81% purity: 98.61% |
| 2 | [structure: 4-NO2 isoindolinone glutamine amide methyl ester] | [structure: 3-(4-nitro-1-oxoisoindolin-2-yl)piperidine-2,6-dione] | yield: 86% purity: 99.21% |
| 3 | [structure: 4-NO2, α-methyl isoindolinone glutamine amide methyl ester] | [structure: 3-methyl-3-(4-nitro-1-oxoisoindolin-2-yl)piperidine-2,6-dione] | yield: 71% purity: 97.97% |

Example 8

The synthesis of 3-[4-(N-benzyloxycarbonyl)amino-1,3-dihydro-1-oxo-2H-isoindol-2-yl]-glutaramide A mixture of dimethyl 3-(4-amino-1,3-dihydro-1-oxo-2H-isoindol-2-yl)-glutarate (30.6 g), anhydrous acetonitrile (150 ml) and triethylamine (13.9 ml) was stirred with benzyl chloroformate (17.1 g) under catalytic amount of MAP under reflux for 4 hours. The reaction mixture was cooled to room temperature and then mixed with water (500 ml). The resulting mixture was then extracted with dichloromethane and dried over anhydrous sodium sulphate, then concentrated under reduced pressure to give a red sticky substance (66 g). The solution of residue in supersaturated methanol-ammonia (250 ml) was stirred at 2530° C. for over 24 hours and white solid was precipitated. Crystal grew in an ice bath for 2 hours. After filter the cake was dried under reduced pressure to give 44.4 g of white crystal.

yield: 67%. mp: 190~192° C.

$^1$H-NMR: (300 MHz, DMSO-$d_6$) δ: 4.29 (d, 1H); 4.56 (d, 1H), 7.56 (s, 1H), 6.59 (d, 1H), 7.34 (t, 1H), 6.88 (d, 1H), 4.70 (m, 1H), 2.01 (m, 2H), 2.20 (m, 1H), 2.02 (m, 1H), 6.59 (s, 1H); 6.74 (s, 1H), 4.38 (s, 2H), 7.14~7.40 (m, 7H).

$^1$H-NMR: (300 MHz, DMSO-$d_6$/$D_2O$) δ: 4.29 (d, 1H); 4.56 (d, 1H), 6.59 (d, 1H), 7.34 (t, 1H), 6.88 (d, 1H), 4.70 (m, 1H), 2.01 (m, 2H), 2.20 (m, 1H), 2.02 (m, 1H), 4.38 (s, 2H), 7.14~7.40 (m, 5H).

FAB(M+1): 443

Test condition of HPLC:

type and specification of column: phenomenex Luna 5u C18

250 mm×4.6 mm; velocity: 1.0 ml/min; λ=230 nm mobile phase: acetonitrile/0.1% phosphate=40/60 appearance time of target yield: 6.980 minutes purity of target yield: 98.67%

With the similar methods, the compounds in the following table are obtained:

| Formula sequence number | starting material | target yield | yield/purity (HPLC by normalization) |
|---|---|---|---|
| 1 | (structure: 4-NO$_2$ isoindolinone with dimethyl glutarate) | (structure: 4-NO$_2$ isoindolinone with glutaramide) | yield: 72% purity: 97.96% |
| 2 | (structure: 4-Cl isoindolinone with dimethyl glutarate) | (structure: 4-Cl isoindolinone with glutaramide) | yield: 75.1% purity: 97.55% |
| 3 | (structure: 4-NO$_2$ isoindolinone, α-methyl, dimethyl glutarate) | (structure: 4-NO$_2$ isoindolinone, α-methyl, glutaramide) | yield: 64.1% purity: 96.74% |

Example 9

The synthesis of 3-(4-amino-1,3-dihydro-1-oxo-2H-isoindol-2-yl)-2,6-dioxopiperidine 3-[4-(N-benzyloxycarbonyl)amino-1,3-dihydro-1-oxo-2H-isoindol-2-yl]-glutaramide (30 g) was stirred with formamide (150 ml) for 3~4 hours by slowly heating up to 160° C. The reaction mixture was cooled to 0° C. and then mixed with water (750 ml). After crystal growing for 1 hour, the resulting mixture was filtered and dried to give 21.6 g of light yellow solid. The solution of this residue in methanol (325 ml) was stirred with 5% Pd/C (0.3 g) and formamide (22 g) at 30° C. for 2 hours. Pd/C was filtered and the filtrate concentrated under reduced pressure to yield a yellow solid. Recrystallization and washing by isopropanol and active carbon gave 12.75 g of light yellow solid. yield: 72%. mp: 251.1~252.4° C.

$^1$H-NMR: (300 MHz, DMSO-$d_6$) δ: 2.02 (m, 2H), 2.01~2.06 (m, 1H), 2.25~2.39 (m, 1H), 2.59~2.64 (m, 1H), 2.83~2.94 (m, 1H), 4.16 (dd, 2H), 5.08 (dd, 1H), 5.35 (s, 2H), 6.80 (d, 1H), 6.93 (d, 1H), 7.90 (t, 1H), 10.91 (s, 1H).

FAB(M+1): 260

Element analysis: theoretical data: C, 60.22%; H, 5.05%; N, 16.21% measured data: C, 60.27%; H, 5.13%; N, 16.26%

Test condition of HPLC:

type and specification of column: phenomenex Luna 5u C18

250 mm×4.6 mm; velocity: 1.0 ml/min; λ=230 nm mobile phase: acetonitrile/0.1% phosphate=10/90 appearance time of target yield: 11.77 minutes purity of target yield: 99.37%

With the similar methods, the compounds in the following table are obtained:

dried under reduced pressure to give 3.7 g of target yield as a white solid. yield: 81%. Melting point test showed that the product began to melt at 90° C. and the final melting point was not apparently observed.

$^1$H-NMR: (300 MHz, DMSO-$d_6$) δ: 2.01 (m, 2H), 2.20 (m, 2H), 3.78 (m, 1H), 4.55 (s, 2H), 5.30 (s, 2H), 6.73 (d, 1H), 6.85 (d, 1H), 7.12 (t, 1H), 10.99 (br, 2H).

$^1$H-NMR: (300 MHz, DMSO-$d_6$/$D_2O$) δ: 1.88 (m, 2H), 2.09 (m, 2H), 3.71 (m, 1H), 4.49 (s, 2H), 6.76 (d, 1H), 6.90 (d, 1H), 7.15 (t, 1H).

| Formula sequence number | starting material | target yield | yield/purity (HPLC by normalization) |
|---|---|---|---|
| 1 | (structure) | (structure) | yield: 83% purity: 98.97% |
| 2 | (structure) | (structure) | yield: 81% purity: 99.03% |
| 3 | (structure) | (structure) | yield: 76% purity: 98.63% |

Example 10

The synthesis of 3-(4-amino-1,3-dihydro-1-oxo-2H-isoindol-2-yl)-glutaric acid

A mixture of dimethyl 3-(4-amino-1,3-dihydro-1-oxo-2H-isoindol-2-yl)-glutarate (5 g) and tetrahydrofuran (14 ml) in 20% potassium carbonate solution (45 ml) was stirred for 5 hours by heating up to 50° C. The aqueous phase was separated and concentrated to dryness under reduced pressure. The concentrate was stirred with methanol (50 ml) for 30 min. After filter, the filtrate concentrated to dryness and was mixed with isopropanol (50 ml) for crystal growing for 2 hours at room temperature. The resulting mixture was filtered and

FAB(M+1): 279

Element analysis: theoretical data: C, 56.11%; H, 5.07%; N, 10.07% measured data: C, 56.20%; H, 5.21%; N, 10.18%

Test condition of HPLC:

type and specification of column: phenomenex Luna 5u C18

250 mm×4.6 mm; velocity: 1.0 ml/min; λ=230 nm mobile phase: acetonitrile/0.1% phosphate=15/85 appearance time of target yield: 5.260 minutes purity of target yield: 98.7%

With the similar methods, the compounds in the following table are obtained:

| Formula sequence number | starting material | raw material | target yield | yield/purity (HPLC by normalization) |
|---|---|---|---|---|
| 1 | [structure: 4-nitro-isoindolinone-N-CH(CO-OMe)-CH2CH2-CO-OMe] | $K_2CO_3/H_2O$ $CH_3OH$ | [structure: 4-nitro-isoindolinone-N-CH(CO-OH)-CH2CH2-CO-OH] | yield: 84% purity: 97.9% |
| 2 | [structure: 4-chloro-isoindolinone-N-CH(CO-OMe)-CH2CH2-CO-OMe] | $K_2CO_3/H_2O$ EtOH | [structure: 4-chloro-isoindolinone-N-CH(CO-OH)-CH2CH2-CO-OH] | yield: 77% purity: 96.7% |
| 3 | [structure: 4-nitro-isoindolinone-N-C(CH3)(CO-OMe)-CH2CH2-CO-OMe] | $K_2CO_3/H_2O$ EtOH | [structure: 4-nitro-isoindolinone-N-C(CH3)(CO-OH)-CH2CH2-CO-OH] | yield: 68% purity: 93.3% |

Example 11

The synthesis 3-(4-amino-1-oxo-1,3-dihydro-2H-isoindol-2-yl)-2,6-dioxopiperidine A mixture of 3-(4-amino-1,3-dihydro-1-oxo-2H-isoindol-2-yl)-glutaric acid (5 g) and urea (1.08 g) in N,N-dimethylformamide (25 ml) was stirred and heated under reflux for 3~4 hours. The reaction mixture concentrated under reduced pressure at 60° C. and then was added into ice water by being stirred rapidly. After filter, the cake was washed with isopropanol. The crude product was recrystallized from isopropanol and active carbon to give 1.4 g of off-white target compound. Yield: 30%. mp: 252.1~254.3° C.

$^1$H-NMR: (300 MHz, DMSO-$d_6$) δ: 2.03 (m, 2H), 2.01~2.07 (m, 1H), 2.26~2.37 (m, 1H), 2.61~2.65 (m, 1H), 2.87~2.96 (m, 1H), 4.17 (dd, 2H), 5.09 (dd, 1H), 5.36 (s, 2H), 6.81 (d, 1H), 6.92 (d, 1H), 7.91 (t, 1H), 10.93 (s, 1H).

$^1$H-NMR: (300 MHz, DMSO-$d_6$/$D_2O$) δ: 2.02~2.05 (m, 1H), 2.32~2.36 (m, 1H), 2.60~2.65 (m, 1H), 2.83~2.88 (m, 1H), 4.17 (dd, 2H), 5.04 (dd, 1H), 6.82 (d, 1H), 6.94 (d, 1H), 7.20 (t, 1H).

FAB(M+1): 260

Element analysis: theoretical data: C, 60.22%; H, 5.05%; N, 16.21% measured data: C, 60.30%; H, 5.20%; N, 16.18%

With the similar methods, the compounds in the following table are obtained:

| Formula sequence number | starting material | target yield | yield/purity (HPLC by normalization) |
|---|---|---|---|
| 1 | [structure: 4-nitro-isoindolinone-N-CH(CO-OH)-CH2CH2-CO-OH] | [structure: 4-nitro-isoindolinone-N-(2,6-dioxopiperidin-3-yl)] | yield: 33% purity: 99.37% |

| Formula sequence number | starting material | target yield | yield/purity (HPLC by normalization) |
|---|---|---|---|
| 2 | 4-chloro-1-oxoisoindolin-2-yl glutaric acid (structure) | 3-(4-chloro-1-oxoisoindolin-2-yl)piperidine-2,6-dione (structure) | yield: 31% purity: 98.55% |

Example 12

The synthesis of 3-[4-(N-benzyloxycarbonyl)amino-1,3-dihydro-1-oxo-2H-isoindol-2-yl]-glutaric anhydride To a stirred mixture of 3-(4-amino-1,3-dihydro-1-oxo-2H-isoindol-2-yl)-glutaric acid (30.6 g) and triethylamine (13.9 ml) in anhydrous acetonitrile (150 ml) was added benzyl chloroformate (17.1 g) and catalytic amount of DMAP under reflux for 4 hours. The resulting mixture was cooled to room temperature and then added into water (500 ml). The mixture was extracted with dichloromethane and dried over anhydrous sodium sulphate. The resulting mixture was concentrated under reduced pressure to give 66 g of red sticky substance. Then the substance was added in acetic anhydride (250 ml) and heated to 50° C., then pyridine (3 ml) was added and reacted at 70° C. for 30 minutes. The reaction mixture was dried by reduced pressure and added anhydrous methyl tert-butyl ether. Refinement gave 30 g of white target yield. yield: 76%.

FAB(M+1): 395

With the similar methods, the compounds in the following table are obtained:

| Formula sequence number | starting material | target yield | yield |
|---|---|---|---|
| 1 | 4-nitro-1-oxoisoindolin-2-yl glutaric acid (structure) | 3-(4-nitro-1-oxoisoindolin-2-yl)glutaric anhydride (structure) | yield: 91% |
| 2 | 4-chloro-1-oxoisoindolin-2-yl glutaric acid (structure) | 3-(4-chloro-1-oxoisoindolin-2-yl)glutaric anhydride (structure) | yield: 87% |
| 3 | 4-nitro-1-oxoisoindolin-2-yl α-methyl glutaric acid (structure) | 3-methyl-3-(4-nitro-1-oxoisoindolin-2-yl)glutaric anhydride (structure) | yield: 85% |
| 4 | 4-nitro-1-oxoisoindolin-2-yl glutaric acid (S-isomer, structure) | (S)-3-(4-nitro-1-oxoisoindolin-2-yl)glutaric anhydride (structure) | yield: 90% |

| Formula sequence number | starting material | target yield | yield |
|---|---|---|---|
| 5 | [structure: 4-nitro-isoindolinone-N-glutamic acid] | [structure: 4-nitro-isoindolinone-N-glutaric anhydride] | yield: 93.3% |

Example 13

The synthesis of 3-[4-(N-benzyloxycarbonyl)amino-1,3-dihydro-1-oxo-2H-isoindol-2-yl]-isoglutamine A mixture of 3-[4-(N-benzyloxycarbonyl)amino-1,3-dihydro-1-oxo-2H-isoindol-2-yl]-glutaric anhydride (30 g) in dry tetrahydrofuran (300 ml) was stirred at 0° C. under supersaturated ammonia for 2 hours. After filter, the cake was washed with ether and dried under reduced pressure at room temperature to give 27.3 g of white solid.

yield: 84%. purity: 95.61%.

FAB(M+1): 428

With the similar methods, the compounds in the following table are obtained:

| Formula sequence number | starting material | target yield | yield/purity (HPLC by normalization) |
|---|---|---|---|
| 1 | [structure: 4-nitro-isoindolinone glutaric anhydride] | [structure: 4-nitro-isoindolinone isoglutamine] | yield: 80% purity: 96.1% |
| 2 | [structure: 4-chloro-isoindolinone glutaric anhydride] | [structure: 4-chloro-isoindolinone isoglutamine] | yield: 78% purity: 94.3% |
| 3 | [structure: 4-nitro-isoindolinone α-methyl glutaric anhydride] | [structure: 4-nitro-isoindolinone α-methyl isoglutamine] | yield: 75% purity: 93.1% |
| 4 | [structure: 4-nitro-isoindolinone glutaric anhydride, chiral] | [structure: 4-nitro-isoindolinone isoglutamine, chiral] | yield: 75% purity: 95.3% |

| Formula sequence number | starting material | target yield | yield/purity (HPLC by normalization) |
|---|---|---|---|
| 5 | (structure: 4-nitro-isoindolinone with dioxopiperidine-dione) | (structure: 4-nitro-isoindolinone glutamine acid) | yield: 79% purity: 94.7% |

Example 14

The synthesis of 3-(4-amino-1-oxo-1,3-dihydro-2H-isoindol-2-yl)-2,6-dioxopiperidine To a stirred mixture of 3-[4-(N-benzyloxycarbonyl)amino-1,3-dihydro-1-oxo-2H-isoindol-2-yl]-isoglutamine (10 g) in DMF (30 ml) was added thionyl chloride (5 g) by droplet at −20° C. for reaction in heat preservation for 2~3 hours. The resulting mixture was mixed in ice water stirred rapidly. Then the mixture was extracted with ethyl acetate (2×50 ml) and dried over anhydrous sodium sulfate. Sodium sulfate was filtered and the filtrate concentrated to dryness under reduced pressure. The concentrate was mixed in methanol (100 ml) and stirred with 5% Pd/C (1 g) and ammonium formate (7 g) at 30° C. for 2 hours. Pd/C was filtered and the filtrate concentrated to dryness. The concentrate was recrystallized from isopropanol and rinsed with water. Decompression drying gave 3.76 g of target yield as a light yellow solid. yield: 62%. mp: 250.8~252.7° C.

$^1$H-NMR: (300 MHz, DMSO-$d_6$/$D_2O$) δ: 2.04~2.10 (m, 1H), 2.34~2.39 (m, 1H), 2.61~2.67 (m, 1H), 2.87~2.91 (m, 1H), 4.18 (dd, 2H), 5.08 (dd, 2H), 6.84 (d, 1H), 6.96 (d, 1H), 7.23 (t, 1H)

FAB(M+1): 260

Element analysis: theoretical data: C, 60.22%; H, 5.05%; N, 16.21% measured data: C, 60.04%; H, 5.31%; N, 16.33%

Test condition of HPLC:
type and specification of column: phenomenex Luna 5u C18
250 mm×4.6 mm; velocity: 1.0 ml/min; λ=230 nm
mobile phase: acetonitrile/0.1% phosphate=10/90
appearance time of target yield: 11.767 minutes
purity of target yield: 99.69%.

Example 15

The synthesis of 3-(4-nitro-1-oxo-1,3-dihydro-2H-isoindol-2-yl)-2,6-dioxopiperidine To a mixture of 3-(4-nitro-1,3-dihydro-1-oxo-2H-isoindol-2-yl)-isoglutamine (9 g) in N,N-dimethylformamide (80 ml), was added thionyl chloride (6.6 g) by droplet below 0° C. for stirred reaction in heat preservation for 2~3 hours. The resulting solution was added by droplet into mixture of ice and water and pH value was adjusted to 7~8 with sodium carbonate. The mixture was stirred for 30 minutes and filtered to get light yellow crude. Refining with methanol gave 6.6 g of target yield as a light yellow solid. yield: 78%.

FAB(M+1): 290

Element analysis: theoretical data: C, 53.98%; H, 3.83%; N, 14.53% measured data: C, 54.06%; H, 3.95%; N, 14.61%

With the similar methods, the compounds in the following table are obtained:

| Formula sequence number | starting material | target yield | yield/purity (HPLC by normalization) |
|---|---|---|---|
| 1 | (structure: 4-Cl-isoindolinone glutamine acid with NH2) | (structure: 4-Cl-isoindolinone dioxopiperidine) | yield: 83% purity: 93.4% |
| 2 | (structure: 4-NO2-isoindolinone with α-methyl glutamine acid) | (structure: 4-NO2-isoindolinone α-methyl dioxopiperidine) | yield: 87% purity: 91% |

| Formula sequence number | starting material | target yield | yield/purity (HPLC by normalization) |
|---|---|---|---|
| 3 | (structure: 4-nitro isoindolinone-N-CH(CH2CH2COOH)-C(=O)NH2) | (structure: 4-nitro isoindolinone with 2,6-dioxopiperidine) | yield: 77% purity: 93.1% |
| 4 | (structure: 4-nitro isoindolinone-N-CH(CH2CH2COOH)-C(=O)NH2) | (structure: 4-nitro isoindolinone with 2,6-dioxopiperidine) | yield: 81% purity: 92.2% |

Example 16

The synthesis of 3-(4-amino-1-oxo-1,3-dihydro-2H-isoindol-2-yl)-2,6-dioxopiperidine A mixture of 3-(4-nitro-1,3-dihydro-1-oxo-2H-isoindol-2-yl)-2,6-dioxopiperidine (7 g), 5% Pd/C (1.4 g) and ammonium formate (2.1 g) in methanol (35 ml) was stirred completely at room temperature for 2 hours. Pd/C was filtered and the filtrate concentrated to dry under reduced pressure. Recrystallization from heated isopropanol and washing with water gave 5.6 g of yellow crystal.

yield: 89%. mp: 252.3~254.0° C.
$^1$H-NMR: (300 MHz, DMSO-$d_6$) δ: 2.00~2.08 (m, 1H), 2.27~2.32 (m, 1H), 2.58~2.64 (m, 1H), 2.86~2.96 (m, 1H), 4.15 (dd, 2H), 5.11 (dd, 2H), 6.80 (d, 1H), 6.91 (d, 1H), 7.19 (t, 1H), 11.00 (s, 1H).
FAB(M+1): 260
Element analysis: theoretical data: C, 60.22%; H, 5.05%; N, 16.21%
measured data: C, 60.17%; H, 5.21%; N, 16.26%
Preparation with the same method:
(R)-3-(4-amino-1-oxo-1,3-dihydro-2H-isoindol-2-yl)-2,6-dioxopiperidine;
yield: 93%; purity 99.41%.
Preparation with the same method:
(S)-3-(4-amino-1-oxo-1,3-dihydro-2H-isoindol-2-yl)-2,6-dioxopiperidine;
yield: 91%; purity: 99.73%.

Example 17

The synthesis of 3-(4-amino-1-oxo-1,3-dihydro-2H-isoindol-2-yl)-2,6-dioxopiperidine A mixture of 3-(4-chloro-1-oxo-1,3-dihydro-2H-isoindol-2-yl)-2,6-dioxopiperidine (5 g) in ammonium formate (30 ml) was stirred by heating up slowly to reflux and then reacted under ammonia for 6~8 hours. The reaction mixture concentrated to dryness under reduced pressure. Recrystallization from heated isopropanol gave 3.96 g of target yield. yield: 85%. Purity: 99.17%. mp: 251.6~253.9° C.

$^1$H-NMR: (300 MHz, DMSO-$d_6$) δ: 2.05~2.11 (m, 1H), 2.25~2.34 (m, 1H), 2.60~2.65 (m, 1H), 2.85~2.97 (m, 1H), 4.16 (dd, 2H), 5.12 (dd, 2H), 6.82 (d, 1H), 6.90 (d, 1H), 7.19 (t, 1H), 10.97 (s, 1H)
FAB(M+1): 260
Element analysis: theoretical data: C, 60.22%; H, 5.05%; N, 16.21%
measured data: C, 60.29%; H, 5.16%; N, 16.27%

Example 18

The synthesis of 3-(4-nitro-1,3-dihydro-1-oxo-2H-isoindol-2-yl)-glutaric acid

A mixture of 4-nitro-2,3-dihydro-1H-isoindol-1-one (80 g) and cesium carbonate (219 g) in triethylamine (100 ml) was stirred for over half an hour. Under nitrogen ethyl chloroformate (68 ml) was added by droplet below 0° C. and reacted by stirring at room temperature for 3~5 hours. The resulting mixture was added in ice water (1000 mL) and then light yellow solid was precipitated. After filter, the cake was washed by iced water. The aqueous phase was extracted with dichloromethane twice and the combined extracts were dried with anhydrous sodium sulphate. After filtered, the filtrate was concentrated to dry under reduced pressure. The concentrated was diluted with n-hexane (120 ml) and stirred to precipitate crystal. Filter and drying under reduced pressure gave light yellow solid.

A mixture of D,L-glutamic acid (66.7 g) in tetrahydrofuran (330 ml) was stirred with the intermediate prepared above in batches at subzero temperature. Triethylamine (6.5 ml) was added in the mixture to react for 20 min and then for 16~24 hours under reflux. The reaction mixture was cooled and filtered. The filtrate was concentrated to dryness under reduced pressure. The concentrate was dissolved in dichloromethane (60 ml) and extracted with saturated sodium bicarbonate solution. When pH of the resulting mixture was adjusted to 2 by 2N hydrochloric acid, a number of light yellow solid was precipitated, subsequently extracted with dichloromethane, and washed with distilled water, dried over anhydrous sodium sulfate, filtered and concentrated under reduced pressure, finally crystal grew by standing, filtered and dried to give 94.2 g of title product as light yellow solid, yield 79%. purity 95.81%.

FAB(M+1): 309.

Element analysis: theoretical data: C, 50.65%; H, 3.92%; N, 9.09% measured data: C, 50.54%; H, 4.01%; N, 9.04%

INDUSTRIAL APPLICABILITY

The present processes have the following advantages:

i. The method for preparing key substrate needed in the synthesis is simple and with low cost, which is suitable for commercial process;

ii. Each step to the present invention is under mild reaction conditions without hard long-time reflux.

iii. The products yielded in each step to the present invention are of high purity, which simplify the extraction and purification process without column chromatography or other complicated extraction conditions.

iv. There is high yield in each reaction. When 3-(4-amino-1-oxo-1,3-dihydro-2H-isoindol-2-yl)-2,6-dioxopiperidine is synthesized from the original raw material, 4-nitro-2,3-dihydro-1H-isoindol-1-one and α-bromodimethyl glutarate, the total yield averages from 35% to 40%. Hence the preparation methods are simple with low costs.

v. Only by three or four procedures can the key product be yielded, which leads to short synthesis routes and simple methods.

vi. The solvents used in each preparation procedure are easy to be disposed for environment protection, which is relatively eco-friendly.

The invention claimed is:

1. A method for synthesizing a compound of Formula (I), comprising:

(1) stirring the following compound of Formula (II)

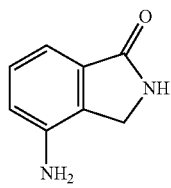 [SMILES: Nc1cccc2c1CNC2=O]

Compound of Formula (II)

in a reaction system in the presence of potassium hydroxide, potassium carbonate, sodium hydroxide, sodium carbonate, cesium hydroxide, or cesium carbonate for a time period of from 5 minutes to 6 hours;

adding the following compound of Formula (III)

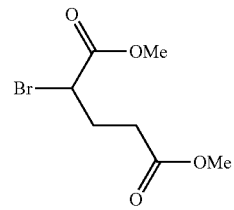 [SMILES: COC(=O)CCC(Br)C(=O)OC]

Compound of Formula (III)

into the reaction system, at a reaction temperature ranging from −20° C. to 80° C., for a reaction time ranging from 1 hour to 72 hours, to yield the following compound of Formula (IV)

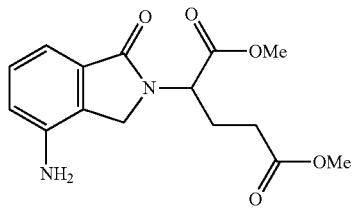

Compound of Formula (IV); and (2) cyclizing the compound of Formula (IV) from step (1) in the presence of lithium amide, sodium amide, or potassamide, at a reaction temperature ranging from −60° C. to 80° C., for a reaction time ranging from 30 minutes to 24 hours, to yield the following compound of Formula (I)

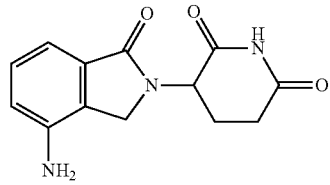 [SMILES: Nc1cccc2c1CN(C1CCC(=O)NC1=O)C2=O]

Compound of Formula (I).

* * * * *

UNITED STATES PATENT AND TRADEMARK OFFICE
CERTIFICATE OF CORRECTION

PATENT NO. : 9,085,530 B2
APPLICATION NO. : 13/375610
DATED : July 21, 2015
INVENTOR(S) : Rong Yan, Hao Yang and Yongxiang Xu It is certified that error appears in the above-identified patent and that said Letters Patent is hereby corrected as shown below:

On the Title Page item (73),

Please correct the Assignee from:

"iangsu" to --Jiangsu--.

Signed and Sealed this
First Day of December, 2015

Michelle K. Lee
*Director of the United States Patent and Trademark Office*